US006941317B1

(12) United States Patent
Chamberlin et al.

(10) Patent No.: US 6,941,317 B1
(45) Date of Patent: Sep. 6, 2005

(54) GRAPHICAL USER INTERFACE FOR DISPLAY AND ANALYSIS OF BIOLOGICAL SEQUENCE DATA

(75) Inventors: Stephen Chamberlin, Alachua; Steven A. Benner, Gainesville, both of FL (US); Lukas Knecht, Zurich (CH)

(73) Assignee: Eragen Biosciences, Inc., Madison, WI (US)

( * ) Notice: Subject to any disclaimer, the term of this patent is extended or adjusted under 35 U.S.C. 154(b) by 0 days.

(21) Appl. No.: 09/397,335

(22) Filed: Sep. 14, 1999

(51) Int. Cl.[7] .................................................. G06F 17/30
(52) U.S. Cl. ........................................ 707/102; 435/6
(58) Field of Search ............................ 707/102; 435/6

(56) References Cited

U.S. PATENT DOCUMENTS

| | | | |
|---|---|---|---|
| 4,704,692 A | 11/1987 | Ladner | |
| 4,710,763 A | 12/1987 | Franke et al. | |
| 4,771,384 A | 9/1988 | Daniels et al. | |
| 4,923,808 A | 5/1990 | Matteucci | |
| 4,939,666 A | 7/1990 | Hardman | |
| 5,146,556 A | 9/1992 | Hullot et al. | |
| 5,187,775 A | 2/1993 | Schroeder et al. | |
| 5,404,442 A | 4/1995 | Foster et al. | |
| 5,436,850 A * | 7/1995 | Eisenberg et al. | ............ 436/86 |
| 5,452,416 A | 9/1995 | Hilton et al. | |
| 5,453,937 A | 9/1995 | Srinivasan et al. | |
| 5,524,240 A | 6/1996 | Barbara et al. | |
| 5,544,352 A | 8/1996 | Egger | |
| 5,557,535 A | 9/1996 | Srinivasan et al. | |
| 5,577,249 A | 11/1996 | Califano | |
| 5,595,877 A | 1/1997 | Gold et al. | |
| 5,598,350 A | 1/1997 | Kawanishi et al. | |
| 5,600,826 A | 2/1997 | Ando | |
| 5,701,256 A | 12/1997 | Marr et al. | |
| 5,706,498 A | 1/1998 | Fujimiya | |
| 5,721,900 A | 2/1998 | Banning et al. | |
| 5,724,253 A | 3/1998 | Skovira | |
| 5,724,605 A | 3/1998 | Wissner | |
| 5,748,927 A | 5/1998 | Stein et al. | |
| 5,761,656 A | 6/1998 | Ben-Schachar | |
| 5,777,616 A | 7/1998 | Bates et al. | |
| 5,795,716 A | 8/1998 | Chee et al. | |
| 5,799,301 A | 8/1998 | Castelli et al. | |
| 5,812,804 A | 9/1998 | Bates et al. | |

(Continued)

FOREIGN PATENT DOCUMENTS

| | | |
|---|---|---|
| WO | 9623078 | 8/1996 |
| WO | 9826407 | 6/1998 |

OTHER PUBLICATIONS

"WWW–Query: An on–line retrievel system for biological sequence banks," G. Perriere et al. *Biochimie*, Paris, Fr. vol. 78, 1996, pp. 364–369, XP001014183.

"TreeView: An application to display phylogenetic trees on personal computers" *Computer Applications in the Biosciences*, 1996, pp. 357–358, XP001010348.

"On The Implementation of a Phylogenetic Tree Data Base" Victoria, BC, Aug. 22–24, 1999 New York NY, IEEE, US., vol. Conf. 7, ISBN: 07803–5583–0.

"A Brief guide to phylogenetic software" Trends in Genetics, NL, Elsevier Science Publishers B.V. Amsterdam, vol. 14, No. 11, Nov. 1, 1998, pp. 473–475, XP004146861.

*Primary Examiner*—Wayne Amsbury
(74) *Attorney, Agent, or Firm*—Gregory T. Pletta

(57) ABSTRACT

A computer research tool is provided for searching and displaying biological data. Specifically, the invention provides a computer research tool for performing computerized research of biological data from various databases and for providing a novel graphical user interface that significantly enhances biological data representation, progressive querying and cross-navigation of windows and databases. The invention can be implemented in numerous ways, including as a system, a device, a method, or a computer readable medium.

42 Claims, 23 Drawing Sheets

U.S. PATENT DOCUMENTS

| | | |
|---|---|---|
| 5,815,151 A | 9/1998 | Argiolas |
| 5,828,376 A | 10/1998 | Solimene et al. |
| 5,842,151 A | 11/1998 | Noguchi |
| 5,856,928 A | 1/1999 | Yan |
| 5,864,488 A | 1/1999 | Isaacs et al. |
| 5,873,052 A | 2/1999 | Sharaf |
| 5,878,373 A | 3/1999 | Cohen et al. |
| 5,884,230 A | 3/1999 | Srinivasan et al. |
| 5,891,632 A | 4/1999 | Imai |
| 5,893,082 A | 4/1999 | McCormick |
| 5,911,138 A | 6/1999 | Li et al. |
| 5,917,492 A | 6/1999 | Bereiter et al. |
| 5,926,806 A | 7/1999 | Marshall et al. |
| 5,977,890 A * | 11/1999 | Riigoutsos et al. ............ 341/55 |
| 5,994,099 A * | 11/1999 | Lewis et al. ................ 435/69.1 |
| 6,068,975 A * | 5/2000 | Gilliam et al. ............ 435/320.1 |
| 6,141,657 A * | 10/2000 | Rothberg et al. ............... 707/6 |
| 6,221,587 B1 * | 4/2001 | Ecker et al. .................... 435/6 |
| 6,223,186 B1 * | 5/2001 | Rigault et al. ............... 707/104 |
| 6,270,971 B1 * | 8/2001 | Ferguson-Smith et al. ...... 435/6 |
| 6,377,893 B1 * | 4/2002 | Benner ........................ 436/86 |

\* cited by examiner

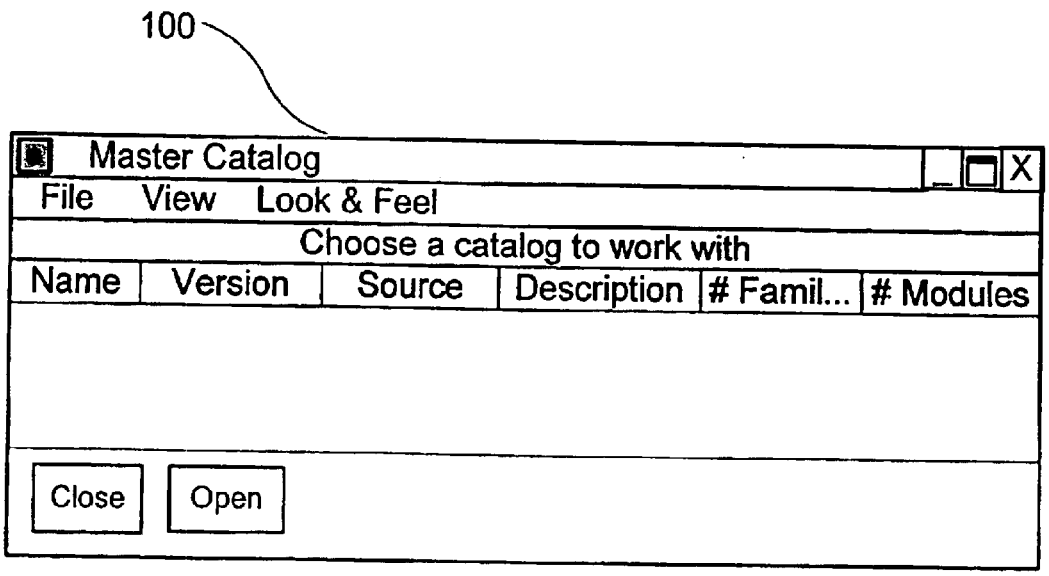

FIG. 7

Catalog Window

This window lists the available catalogs.

Each catalog is a view of relationships between (some or all of) the protein sequences in the database. Different catalogs emphasize different features of the protein sequence database. (For example, one catalog might emphasize repeat units within proteins, another catalog focuses on alignments which comprise the whole length of genes (the gene product catalog), and another focuses on local patterns of divergence between protein sequences (the modularized catalog). Catalogs are composed of families of modules, each module defining a region of a protein sequence. Thus, the families relate regions of different protein sequences in biologically meaningful ways.

Double clicking on one of the available catalogs displays a query window for that catalog. Alternatively, you can select a catalog entry with the mouse and click on the Open button on the toolbar.

Note: There is a special catalog, "the Sequence Entry Catalog" that contains just the individual protein sequences. This catalog does not have family names or allow you to search sequences -- it provides direct access to individual protein sequences and can be searched by keyword.

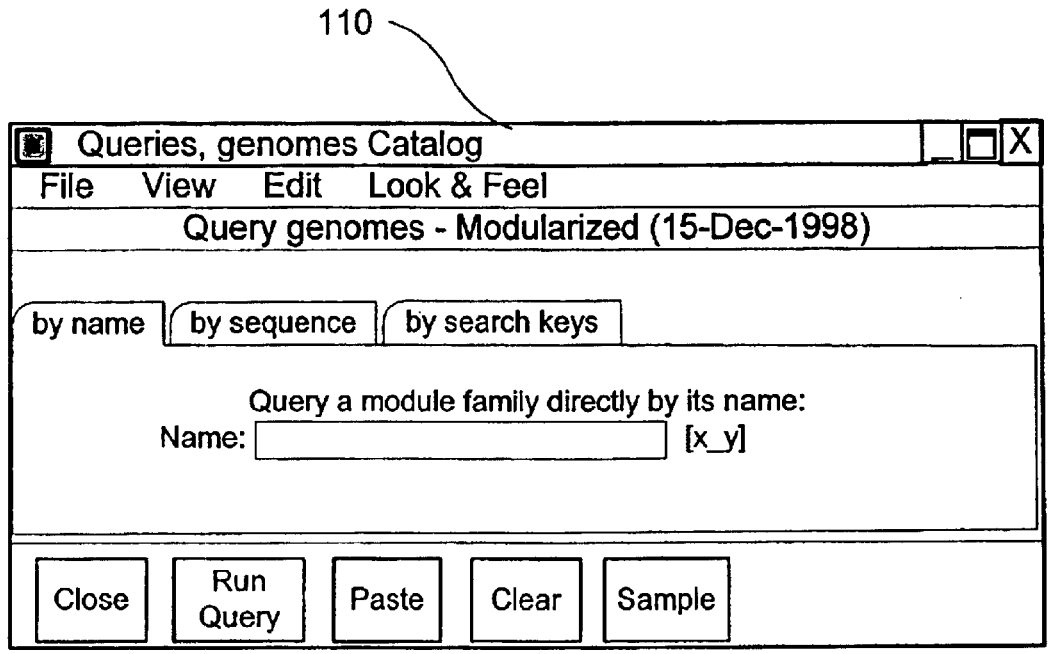

FIG. 8

Query Window

The query window provides several different ways to search the chosen catalog: by catalog family identifier, by keyword, and by sequence. Not all of these methods are available for every catalog.

Search by Family Identifier

Each family in a catalog has a unique identifier that defines a particular family. (These family names area generated automatically when each catalog is built from the protein sequence data.) This search window allows you to obtain a specific family number of interest. The result of this search is the family window showing a graphical view of the associated proteins and their modules.

/140

| # | ID | Description | AA range | genomes (the family's) |
|---|---|---|---|---|
| 1 | mthe_1511 | conserved protein | 129-199 | 357_1 358_1 359_1 |
| 2 | pyro_1912 | 406aa long hypotheti... | 281-341 | 978_1 357_1 358_1 359_1 |
| 3 | mthe_246 | conserved protein | 73-133 | 357_1 358_1 359_1 |
| 4 | aful_1775 | conserved hypotheti... | 67-127 | 357_1 358_1 359_1 |
| 5 | ecoli_2379 | predicted coding region | 122-182 | 377_1 358_1 378_1 |
| 6 | hinf_744 | glucokinase regulator | 128-188 | 377_1 358_1 378_1 |
| 7 | bsub_170 | predicted coding region | 126-186 | 377_1 358_1 378_1 |
| 8 | hinf_1450 | polysialic acid cap... | 106-164 | 371_1 358_1 370_1 372_1 |

Title: 358_1 Module Family, genomes Catalog
File  View  Catalogs

Buttons: Close | Print | Export | MSA | Tree    with: (none)    ☐ Propagate

FIG. 9

Family Window

The family window is the gateway to navigational power of MasterCatalog. The window shows all of the sequences in the currently selected catalog that are members of that family. It shows the location of the modules in each of the sequences for the family (in red), and it also shows the location of all other modules in those sequence.

You can perform many different tasks from this point:

1. Display the multiple sequence alignment of the current family.

Selecting the MSA button on the window's toolbar shows the multiple sequence alignment (the way in which the modules are related at the amino acid level)

2. Display the evolutionary tree of the current family

Selecting the Tree button on the window's shows the evolutionary tree. This indicates the pattern of divergence/similarity between individual modules, assuming that the distance between modules can be computed from the similarity in the protein sequences.

3. Display protein sequence information for any member of family.

Double clicking on any sequence in the ID column shows the protein sequence window for that family (including catalog membership, description, and annotations).

4. Select sequences/modules

You can select some or all of the modules possessed by individual sequences. Modules are selected individually in the summary display with single mouse clicks. All of the modules possessed by a protein can be selected at once by selecting the module id (#) on the left-hand column.

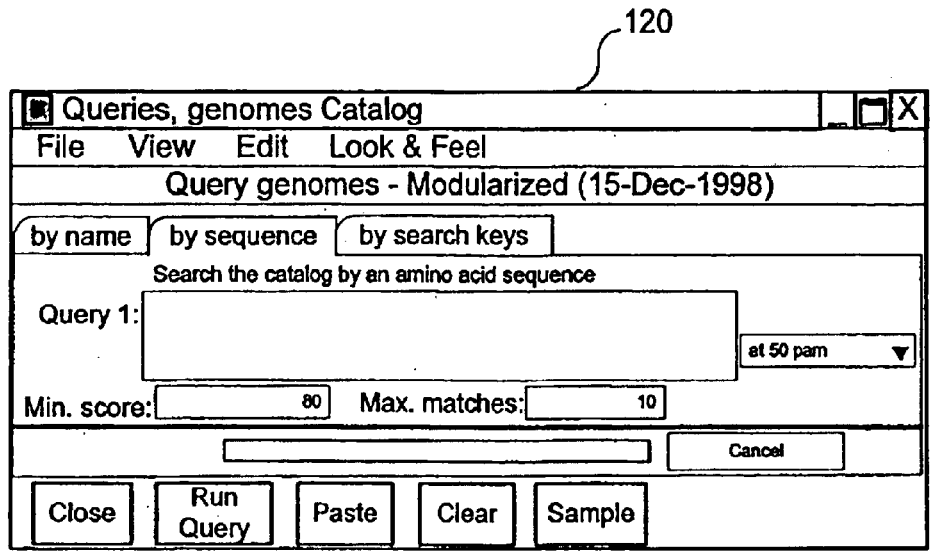

FIG. 10A

Search by Sequence

This window allows you to search a protein against a catalog for homologous (evolutionary related) protein families. The result of this search is a sequence search summary window showing a graphical view of the relationship between the probe sequence and the associated families.
Note: This search can take as long as minutes for large probe sequences. You can abort the search at any time with the cancel button.

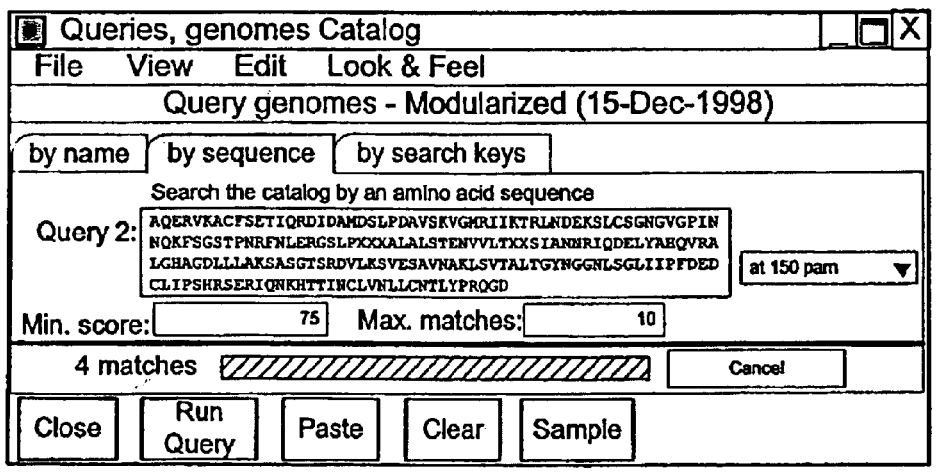

FIG. 10B

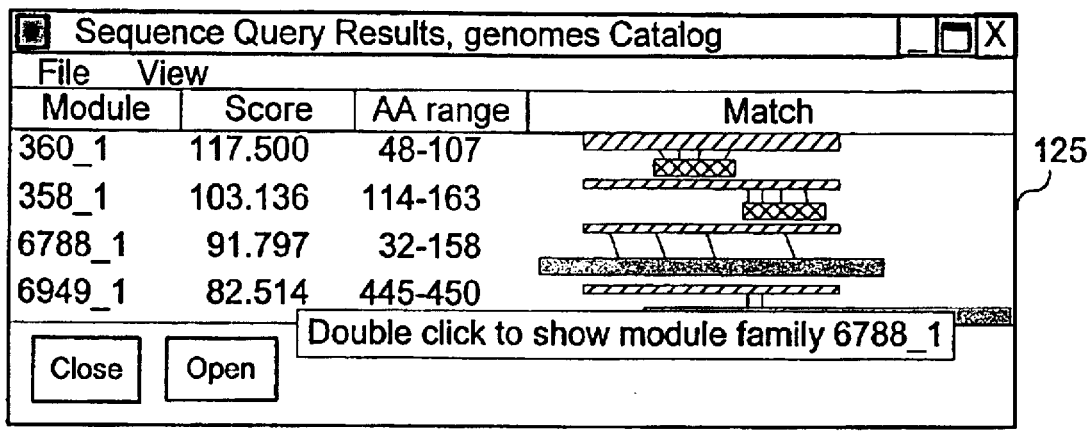

FIG. 11

Sequence search results

This window shows the relationship between the probe sequence chosen for the query and each of the families that are related. The score corresponds to a "log odds score," the probability that the relationship between the sequence is related according to the model of evolution versus the probability that the similarity is by chance.

Double-clicking on any module shown in this summary will display the summary window for that family. The alignment of the probe sequence with the summary can then be displayed.

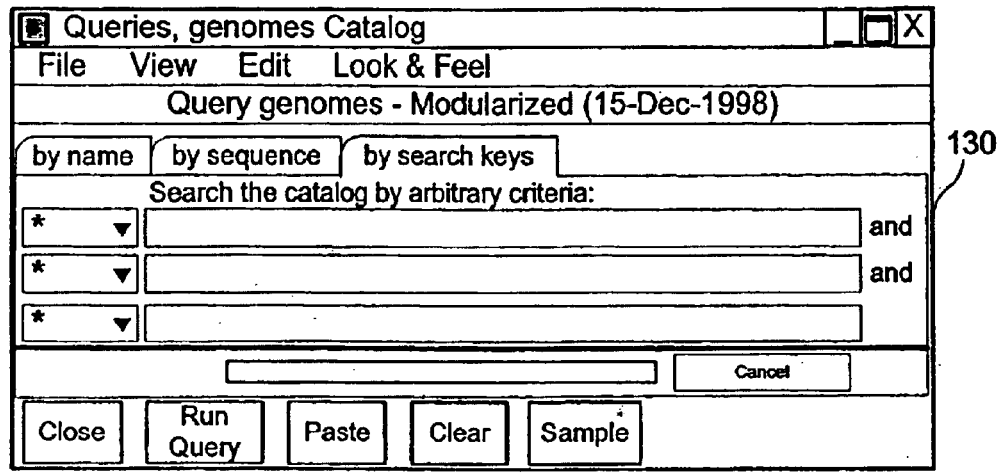

FIG. 12

Search by Keyword

This window provides searches of the protein sequence database by keyword, according to annotations of proteins in the original sequence database. Keywords provided include selection by organism, by classification, by gene name and by gene product description. The result of this search is a sequence summary window showing a graphical view of individual protein sequences which fit the keyword search criteria.

Search results window

These windows summarize the search results for search by sequence and search by keyword, respectively.

135
```
┌─────────────────────────────────────────────────────────────┐
│ ▣  Keyword Query Results, genomes Catalog          _ □ X   │
├─────────────────────────────────────────────────────────────┤
│ File   View                                                 │
├──────────┬──────────────────┬──────┬──────────────────────┤
│    ID    │   Description    │  AA  │      Modules         │
├──────────┼──────────────────┼──────┼──────────────────────┤
│ aful_79    │ acetylornithine ami...│ 375 │ —175_1——1753_1—1754 │
│ BIOA_BACSH │ ADENOSYLEMET...       │ 455 │ ——not modularized— │
│ BIOA_ERWHE │ ADENOSYLEMET...       │ 429 │ ——not modularized— │
│                          ●                                  │
│                          ●                                  │
│                          ●                                  │
│ ┌───────┐                                                   │
│ │ Close │                                                   │
│ └───────┘                                                   │
└─────────────────────────────────────────────────────────────┘
```

FIG. 13

Keyword search results

The keyword search results window shows the sequences. For each sequence all modules are shown for the currently selected catalog. Note: In some cases, sequences may match with a particular keyword but no modularization information is available because these sequences were not part of the set included in the currently selected catalog.

Double-clicking on any module shown in the search results will display the summary window for the associated family.

Queries, genomes Catalog

File  View  Edit  Look & Feel

Query genomes - Modularized (15-Dec-1998)

by name | by sequence | by search keys

Search the catalog by an amino acid sequence

Query 2:
```
AQERVKACFSETIQRDIDAMDSLPDAVSKVGMRIIKTRLNDEKSLCSGNGVGP
INNQKFSGSTPNRFNLERGSLPXXXALALSTENVVLTXXSIANNRIQDELYAH
QVRALGHAGDLLLAKSASGTSRDVLKSVESAVNAKLSVTALTGYNGGNLSGLI
IPFDEDCLIPSHRSERIQNKHTTINCLVNLLCNTLYPRQGD
```
at 150 pam ▼

Min. score: 75   Max. matches: 10

4 matches [////////////////////]   Cancel

Close | Run Query | Paste | Clear | Sample

— 120

Sequence Query Results, genomes Catalog

File  View

| Module | Score | AA range | Match |
|--------|-------|----------|-------|
| 360_1  | 117.500 | 48-107  | [360_1] |
| 358_1  | 103.136 | 114-163 | [358_1] |
| 6788_1 | 91.797  | 32-158  |        |
| 6949_1 | 82.514  | 445-450 |        |

Close | Open

125

358_1 Module Family, genomes Catalog

File  View  Catalogs

| # | ID | Description | AA range | genomes (the family's) |
|---|----|-----|-----|-----|
| 1 | mthe_1511 | conserved protein | 129-199 | —[357_1] [358_1] [359_1] |
| 2 | pyro_1912 | 406aa long hypotheti... | 281-341 | [978_1] [357_1] [358_1] [359_1] |
| 3 | mthe_246 | conserved protein | 73-133 | —[357_1] [358_1] [359_1]— |
| 4 | aful_1775 | conserved hypotheti... | 67-127 | [357_1] [358_1] [359_1] |
| 5 | ecoli_2379 | predicted coding region | 122-182 | [377_1] [357_1] [378_1]— |
| 6 | hinf_744 | glucokinase regulator | 128-188 | —[377_1] [358_1] [378_1] |
| 7 | bsub_170 | predicted coding region | 126-186 | [377_1] [358_1] [378_1] |

Close | Print | Export | MSA | Tree | with: (none) ▼ | ☐ Propagate

GRAPHICAL USER INTERFACE FOR DISPLAY AND ANALYSIS OF BIOLOGICAL SEQUENCE DATA

CROSS-REFERENCE TO RELATED APPLICATIONS

This application claims priority from provisional application Ser. No. 60/154,149, filed Sep. 14, 1999 entitled, "Graphical User Interface for Display and Analysis of Biological Data," the disclosure of which is incorporated herein by reference in its entirety.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

The present invention relates to a computer research tool for searching and displaying biological data. More specifically, the invention relates to a computer research tool utilizing a novel graphical user interface (GUI) for performing computerized research of biological data from various databases and for providing enhanced graphical representation of biological data, progressive querying, and cross-navigation of relational data.

2. Description of the Related Art

Trillions of pieces of information generated by emerging technologies in molecular biology and genetics are stored digitally in computer databases worldwide. In fact, every day approximately 2000 nucleotide sequences are deposited in publicly accessible databases. With such a large amount of multidimensional data, researchers rely on complex information systems to find, summarize and interpret this biological information. This has resulted in the creation of a new field of science known as bioinformatics which combines the power of biochemistry, mathematics, and computers. Bioinformatics has allowed the development of new databases and computational technologies to help in the understanding of the biological meaning encoded in vast collections of sequence data.

A. Biochemistry Overview

An understanding of the biological meaning of sequence data begins with a study of the 20 amino acids that make up proteins. Deoxyribonucleic acid (DNA) contains the blueprints for these structures. DNA is composed of very long polymers of chemical sub-units known as nucleotides. Each nucleotide includes one of four nitrogenous bases: adenine (A), thymine (T), cytosine (C) and guanine (G). DNA serves as a template for ribonucleic acid (RNA), which serves as a template for proteins. Like DNA, RNA is also composed of nucleotides. Each RNA nucleotide includes one of four nitrogenous bases. These bases of RNA differ from that of DNA only in the substitution of thymine (T) with uracil (U). Three nucleotides of DNA encode three nucleotides of RNA, which in turn encode one amino acid of a protein.

Proteins are macromolecules of amino acids which show great diversity in physical properties thereby fulfilling a broad range of biological functions (i.e., polymers of covalently bonded amino acids). A protein's structure and function depends upon its amino acid sequence, which is determined by the nucleotide sequence of the RNA which produced it, which is determined by the nucleotide sequence of the DNA that produced the RNA. Hence, the great diversity observed in the sequence of amino acids is the direct result of the many possible permutations of DNA and RNA. The primary structure is the sequence of amino acids covalently bonded together. The secondary structure is the result of amino acid sequence of the polypeptide. The bonding causes the chain to develop specific shapes (alpha helix, beta sheet). The tertiary structure is the 3-dimensional folding of the alpha helix or the pleated sheet. The quaternary structure is the spatial relationship between the different polypeptides in the protein.

B. Sequence Comparison

Sequence comparison is a very powerful tool in molecular biology, genetics and protein chemistry. Frequently, it is unknown for which proteins a new DNA sequence codes or if it codes for any protein at all. If you compare a new coding sequence with all known sequences there is a high probability to find a similar sequence. Usually one tries to determine what level of similarity is shared between the proteins in terms of structural and functional characteristics. This determination is made by comparing the amino acid sequences of the proteins. It has been observed that the primary structures of a given protein from related species closely resemble one another. Comparisons of the primary structures of homologous proteins (evolutionarily related proteins) indicate which of the proteins' amino acid residues or domains (i.e., stretches of amino acids) are essential to its function, which are of lesser significance, and which have little specific function. Sequences which are found in similar positions of functionally similar proteins are said to be homologous, conservatively substituted or highly conserved. A popular computational tool for rapid comparison of a search sequence to a database of known sequences is the BLAST search. The advantage of a BLAST search is the ability to find matches to distantly related sequences. The disadvantage is that the searches become computationally intensive and may take an inordinate length of time.

C. Biological Databases

In order to perform these sequence comparisons, databases of known biological data need to be accessed. There are a lot of different databanks (databases) where biological information such as DNA and protein sequence data are stored, including, general biological databanks such as EMBL/GENBANK (nucleotide sequences), SWISS-PROT (protein sequences), and PDB/Protein Data Bank (protein structures). [See, e.g., "Comprehensive, Comprehensible, Distributed and Intelligent Databases: Current Status" by Frishman, et al. *Bioinformatics Review*, Vol. 14, No. 7, 1998, pgs. 551–561, incorporated herein by reference]. Specifically, GenBank is an annotated collection of all publicly available DNA sequences. As of August 1999, there were approximately 3,400,000,000 bases in 4,610,000 sequence records. The GenBank database comprises the DNA DataBank of Japan (DDBJ), the European Molecular Biology Laboratory (EMBL), and GenBank at NCBI. SWISS-PROT is an annotated protein sequence database maintained by the Department of Medical Biochemistry of the University of Geneva. The PDB/Protein Data Bank, maintained by Brookhaven National Laboratory, contains all publicly available solved protein structures. These databases contain large amounts of raw sequence data which can be cumbersome to use.

In an effort to provide a more useful form of biological data, there are a number of derived or structured databases which integrate information from multiple primary sources, and may include relational/cross-referenced data with respect to sequence, structure, function, and evolution. A derived database generally contains added descriptive materials on top of the primary data or provides novel structuring of the data based on certain defined relationships. Derived/structured databases typically structure the protein sequence data into usable sets of data (tables), grouping the protein sequences by family or by homology domains. A protein family is a group of sequences that can be aligned from end to end and are <55% different globally. A homologous domain is a subsequence of a protein that is distinguished by a well-defined set of properties or characteristics and may also occur in at least two different subfamilies.

An example of a structured database is ProDom, a protein domain database, consisting of an automatic compilation of homologous domains. The database was designed as a tool to help analyze domain arrangements of proteins and protein families. Current versions of the ProDom database are built using a procedure based on recursive PSI-BLAST searches. ProDom contains 57,976 domain families, sorted by decreasing number of protein sequences in the families. ProDom is generated from the SWISS-PROT database by automated sequence comparison.

Similarly, DOMO is a database of homologous protein domain families. DOMO was obtained from successive sequence analysis steps including similarity search, domain delineation, multiple sequence alignment, and motif construction. DOMO has analyzed 83,054 non redundant protein sequences from SWISS-PROT and PIR-International Sequence DataBase yielding a database of 99,058 domain clusters into 8,877 multiple sequence alignments.

Another derived protein sequence database is the Block Database. Blocks are multiply aligned ungapped segments corresponding to the most highly conserved regions of proteins. The blocks for the Block Database are made automatically by looking for the most highly conserved regions in groups of proteins documented in the Prosite Database. The blocks are then calibrated against the SWISS-PROT database to obtain a measure of the chance distribution matches.

D. Researching Biological Databases

Typically biological databases may be searched by either an unstructured (keyword) or structured (field based) search. An unstructured search of the database is performed by searching for a keyword or the ID of records. For example, a keyword search of "ecoli" retrieves a list of protein sequences that are identified by the keyword "ecoli". A structured search is a more deliberate search, allowing, for example, the searching of the database for protein sequences which contain a particular sequence of interest.

An example of a well known search engine to conduct research on the GenBank database is the ENTREZ search engine which utilizes keyword searching. If a search results in too many hits, ENTREZ allows the addition of new search terms to progressively narrow the number of hits. A researcher may then select all or a subset of the entries that match the search for display to generate a summary page that reports on each of the selected entries. The search results may be displayed in a variety of formats or standardized reports. The form that most biologists are familiar with, the GenBank report, shows the raw GenBank entry. Other familiar formats include FASTA and ASN.1. The genomes division of ENTREZ has a graphic interface based on alignments among multiple maps. The display image shows a series of genetic and physical maps published from a variety of sources, roughly aligned, with diagonal lines connecting common features.

Another search system is SRS (Sequence Retrieval System) which is a Web-based system for searching among multiple sequence databases supported by EMBL. The SRS cross-references sequence information from approximately 40 other sequence databases including ones that hold protein and nucleotide sequence information, 3D structure, disease and phenotype information, and functional information. The SRS search allows structured queries on one or more databases with common fields (e.g., ID, AccNumber, Description). SRS displays the results as a series of hypertext links. The search can be broadened to other databases by bringing in cross-references.

A number of patents exist which relate to display and analysis of biological sequence data, including, U.S. Pat. Nos. 5,891,632; 5,884,230; 5,878,373; 5,873,052; 5,873,052; 5,864,488; 5,856,928; 5,842,151; 5,799,301; 5,795,716; 5,724,605; 5,724,253; 5,706,498; 5,701,256; 5,600,826; 5,598,350; 5,595,877; 5,577,249; 5,557,535; 5,524,240; 5,453,937; 5,187,775; 4,939,666; 4,923,808; 4,771,384; and 4,704,692; and PCT Patent No. WO96/23078; all of which are incorporated herein by reference.

E. Graphical User Interfaces (GUIs)

The development and proliferation of GUIs has greatly enhanced the ease with which users interact with biological databases both in the searching stage and in the display of information. A conventional GUI display includes a desktop metaphor upon which one or more icons, application windows, or other graphical objects are displayed. Typically, a data processing system user interacts with a GUI display utilizing a graphical pointer, which the user controls with a graphical pointing device, such as a mouse, trackball, or joystick. For example, depending upon the actions allowed by the active application or operating system software, the user can select icons or other graphical objects within the GUI display by positioning the graphical pointer over the graphical object and depressing a button associated with the graphical pointing device. In addition, the user can typically relocate icons, application windows, and other graphical objects on the desktop utilizing the well known drag-and-drop techniques. By manipulating the graphical objects within the GUI display, the user can control the underlying hardware devices and software objects represented by the graphical objects in a graphical and intuitive manner.

User interfaces used with multi-tasking processors also allow the user to simultaneously work on many tasks at once, each task being confined to its own display window. The interface allows the presentation of multiple windows in potentially overlapping relationships on a display screen. The user can thus retain a window on the screen while temporarily superimposing a further window entirely or partially overlapping the retained window. This enables the user to divert the attention from a first window to one or more secondary windows for assistance and/or references, so that overall user interaction may be improved. There may be many windows with active applications running at once. Oftentimes, the windows may be (dynamically or statically) related such that modifying a query in one window results in changes to the displayed data in the other related windows, thereby "propagating" the changes throughout.

There are a number of patents which relate to Graphical User Interfaces. For example, the following patents which relate to Graphical User Interfaces, albeit not for biological data, are incorporated by reference herein: U.S. Pat. No. 5,926,806 to Marshall et al.; U.S. Pat. No. 5,544,352 to Egger; U.S. Pat. No. 5,777,616 to Bates et al.; U.S. Pat. No. 5,812,804 to Bates et al.; U.S. Pat. No. 5,146,556 to Hullot et al.; U.S. Pat. No. 5,893,082 to McCormick; U.S. Pat. No. 5,815,151 to Argiolas; U.S. Pat. No. 5,911,138 to Li; U.S. Pat. No. 5,761,656 to Ben-Shachar; U.S. Pat. No. 5,404,442 to Foster et al.; U.S. Pat. No. 5,917,492 to Bereiter et al.; U.S. Pat. No. 4,710,763 to Franke et al.; U.S. Pat. No. 5,828,376 to Solimene et al.; U.S. Pat. No. 5,748,927 to Stein et al.; U.S. Pat. Nos. 5,452,416 to Hilton et al.; and 5,721,900 to Banning.

F. Graphical User Interfaces for Biological Data Systems

As in most industries, software user interfaces for biological data have evolved from the former DOS text and command line interfaces to intuitive screen graphics which represent data in a user friendly manner. In order to evaluate and analyze data sequences from various biological databases, researchers often utilize graphical user interfaces to view biological data in a variety of ways, including multiple sequence alignments (MSAs), secondary structure predictions, two-dimensional graphical representations of sequences, and phylogenetic trees.

A multiple sequence alignment displays the alignment of homologous residues among a set of sequences in columns. In a 2D graphical representation, sequences are displayed as schematic boxes wherein each box is spatially oriented. Phylogenetic trees are genealogical trees which are built up with information gained from the comparison of the amino acid sequences in a protein. The phylogenetic tree (rooted or unrooted) is a graphical representation of the evolutionary distance between individual protein sequences in a family of proteins. The branches of the phylogenetic tree are evolutionary distances from the PAM matrix, an evolutionary model that assumes that estimation of mutation rates for closely related proteins can be extrapolated to distant relationships.

A good example of a graphical user interface can be found in the ProDom interface. The output from a ProDom query for proteins sharing a homologous domain with a particular sequence may be displayed as 2D graphic representations, summarized alignments and trees, alignment in MSF format, and 3D structures. Specifically, the 2D graphical view presents domain arrangements for proteins sharing homology by showing each protein on a single line, starting with its name, hypertext-linked to SWISS-PROT, followed by a 2D view of schematic boxes, each box hypertext-linked to corresponding ProDom entries.

The limitation of most of these systems is that the graphical displays are both static and unrelated. A static graphical display is defined as when a user is unable to refine or modify the search criteria from within the graphical display. Unrelated graphical displays are defined as when a user modifies a graphical display for a particular search, the remaining graphical displays for the particular search are not correspondingly modified (i.e., no propagation). These limitations can make the analysis of protein sequences cumbersome and time consuming. Additionally, the inflexibility of these system could result in an incorrect or incomplete analysis by limiting a user's ability to view all possible relationships.

Accordingly, there is a need in the art for a user friendly computerized research tool for biological data to provide more effective ways to retrieve and view interrelated information from a database. This system needs to provide a usable display for representing vast amounts of discrete information, permitting researchers to focus on the most relevant materials and discover new functional relationships.

To effectually and efficiently analyze the information, there remains a need for a graphical user interface which provides increased flexibility by permitting the user to view any number of related or unrelated data displays from one or more databases at the same time. These displays need to be interlinked such that the selection of one or more entries in one of the display windows causes the other display windows to distinguishably display and act on those entries related to the selection. Progressive querying is also needed to allow the user to quickly discover new relationships based on the results of previous queries.

The present invention is designed to address these needs.

SUMMARY OF THE INVENTION

Broadly speaking, the invention is a computer research tool for searching and displaying biological data. Specifically, the invention provides a computer research tool for performing computerized research of biological data from various databases and for providing a novel graphical user interface that significantly enhances biological data representation, progressive querying and cross-navigation of windows and databases.

The invention can be implemented in numerous ways, including as a system, a device, a method, or a computer readable medium. Several embodiments of the invention are discussed below.

As a computer system, an embodiment of the invention includes a database containing tables of data, a display device and a processor unit. The display device has a plurality of display areas (windows). The processor unit operates to access the database to retrieve the data from the corresponding associated tables and then display the retrieved data in the display areas. The processor unit also detects when a selection associated with one of the display areas is made and thereafter automatically modifies the data being displayed in the other display areas in accordance with the selection. Selection is made in a graphically distinct manner. Changes in certain selections, including scale and limits, propagate throughout.

As a graphical user interface (GUI) for a display screen of a computer, an embodiment of the invention includes a number of display areas ("windows") for searching and displaying biological data which are interlinked for ease of navigation. A variety of formats for searching and displaying biological data is provided. Searches can be performed by keyword, sequence listing or family identifier (module ID). Sequence search results are graphically displayed showing the relationship between the probe sequence chosen for the query and each of the families that are related with their associated modules. Keyword search results are graphically displayed showing all sequences having the requested keyword along with all modules for the currently selected catalog. The module of interest may then be selected which results in a summary window for the family associated with the module. The family summary window display provides a two dimensional spatial orientation of the biological data, including visual locations of modules (represented as schematic boxes) in each of the sequences for a selected family distinguishably displayed and positionally aligned as well as the location of all other modules in those sequences. Another results display provides the user with the associated multiple sequence alignment of biological data and secondary structure predictions (Vparse, Score, PredSI, PredSec). A further results display provides the user with the associated phylogenetic tree (rooted or unrooted). A further display provides the actual protein sequence information for any selected member of a family.

As a method of displaying data on a display device of a computer system, the data being obtained from a relational database associated with the computer system, the display having "windowing" capability to provide a plurality of display areas, an embodiment of the invention includes the operations of: interlinking display areas via the database such that selections may be propagated throughout. The method further includes multiple catalog views, browsing through families, cross-navigation and propagation through all catalogs and sequences, propagation through families, assigning protein function, and scaling of silent/express mutation ratios.

As a computer readable media containing program instructions for displaying data on a display device of a computer system, the data being obtained from a relational database associated with the computer system, the display having "windowing" capability to provide a plurality of display areas, an embodiment of the invention includes: computer readable code devices for interlinking display areas via the database such that selections may be propagated throughout, multiple catalog views, browsing through families, cross-navigation and propagation through all catalogs and sequences, propagation through families, assigning protein function, and scaling of silent/express mutation ratios (kA/kS).

The advantages of the invention are numerous. One significant advantage of the invention is that it allows a user to directly use the data returned by one or more queries as the basis for making additional queries. By this kind of interactive and progressive query-making activity, access to all of the information on a given topic is possible. As a result, new data connections and relationships may be discovered. The user is able to more efficiently and effectively review related biological information than conventionally possible.

All patents, patent applications, provisional applications, and publications referred to or cited herein, or from which a claim for benefit of priority has been made, are incorporated herein by reference in their entirety to the extent they are not inconsistent with the explicit teachings of this specification.

BRIEF DESCRIPTION OF THE DRAWINGS

FIG. 7 depicts a sample screen display for the catalog selection window.

FIG. 8 depicts a sample screen display for the search by name window.

FIG. 9 depicts a sample screen display for the Module Family Summary (MFS) window.

FIG. 10 depicts a sample screen display for the search by sequence window.

FIG. 11 depicts a sample screen display for the sequence search results (SSR) window.

FIG. 12 depicts a sample screen display for the search by keyword window.

FIG. 13 depicts a sample screen display for the keyword search results (KSR) window.

FIG. 16 depicts an example of consecutive screen displays for interactive and progressive query-making activity from search by sequence.

FIG. 17 depicts an example of consecutive screen displays for interactive and progressive query-making activity from search by keyword.

FIG. 18B depicts the MFS window with a second catalog selected and consecutive screen displays for interactive and progressive query-making activity from this window.

FIG. 20 depicts the screen displays showing interactive and progressive query-making activity across multiple MFS windows.

DETAILED DESCRIPTION OF THE PREFERRED EMBODIMENT

Figure 1:
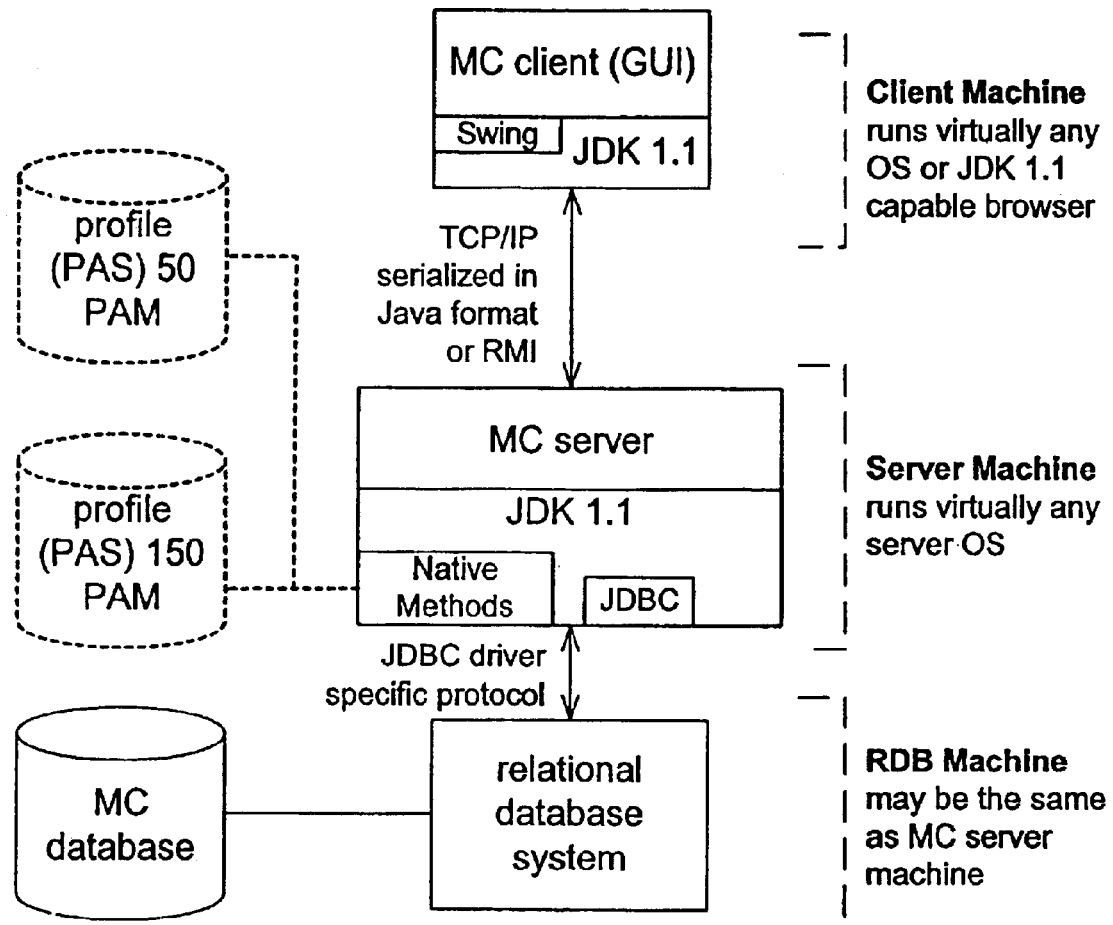
FIG. 1 is an overview of the preferred embodiment of the hardware architecture for computerized searching of biological data.

Referring now to the drawings, the preferred embodiment of the present invention will be described.

I. Architecture

Figure 2:
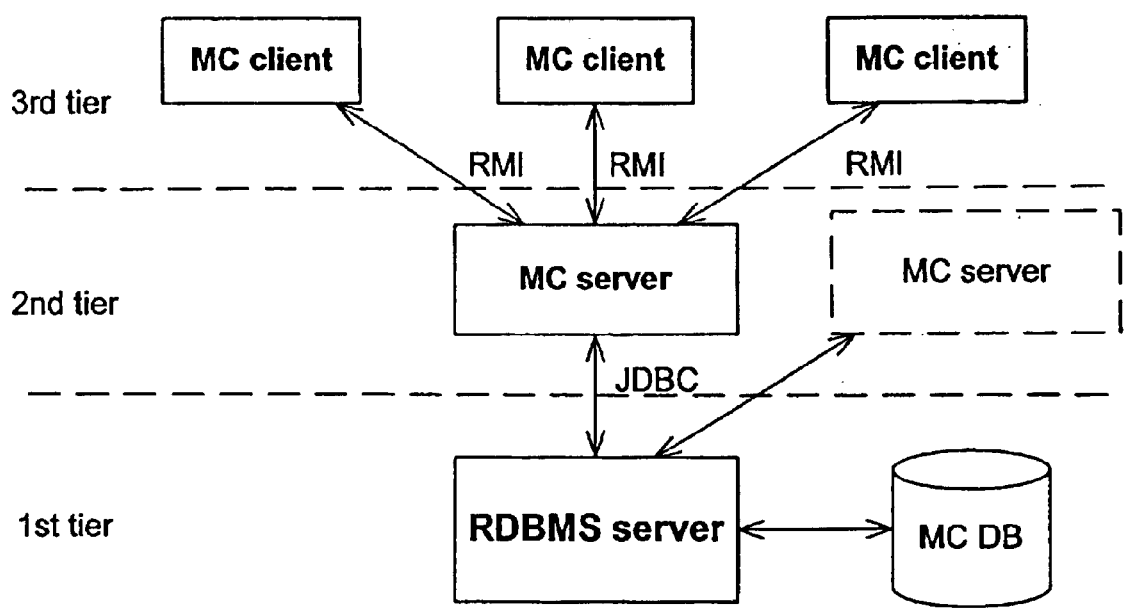
FIG. 2 depicts a classic three tier client server model utilized in a preferred embodiment of the present invention (1-tier/Database Server, 2-tier/Application Server, 3-tier/Client).

FIG. 1 is an overview of the preferred embodiment of the hardware architecture for computerized searching of biological data. The architecture preferably comprises at least two networked computer processors (client component and server component(s)) and a database(s) for storing biological data. The computer processors can be processors that are typically found in personal desktop computers (e.g., IBM, Dell, Macintosh), portable computers, mainframes, minicomputers, or other computing devices. Preferably in the networked client/server architecture of the present invention, a classic three tier client server model is utilized as shown in FIG. 2 (1-tier/Database Server, 2-tier/Application Server, 3-tier/Client). Preferably, a relational database management system (RDMS), either as part of the Application Server component or as a separate component (RDB machine) provides the interface to the database.

In a preferred database-centric client/server architecture, the client application generally requests data and data-related services from the application server which makes requests to the database server. The server(s) (e.g., either as part of the application server machine or a separate RDB/relational database machine) responds to the client's requests and provides secured access to shared data.

II. Client

More specifically, the client components are preferably complete, stand-alone personal computers offering a full range of power and features to run applications. The client component preferably operates under any operating system and includes communication means, input means, storage means, and display means. The user enters input commands into the computer processor through input means which could comprise a keyboard, mouse, or both. Alternatively, the input means could comprise any device used to transfer information or commands. The display comprises a computer monitor, television, LCD, LED, or any other means to convey information to the user. In a preferred embodiment, the user interface is a graphical user interface (GUI) written and operating under the Java programming language (Sun Microsystems) as a Java compatible browser or Java Virtual Machine (JVM). The GUI provides flexible navigational tools to explore patterns in the evolutionary relationships between genomic sequences. The clients and the Application server communicate via Java's RMI (Remote Method Invocation).

III. Server

The server component(s) can be a personal computer, a minicomputer, or a mainframe and offers data management, information sharing between clients, network administration and security. The Database Server (RDBMS—Relational Database Management System) and the Application Server may be the same machine or different hosts if desired. The Application Server is preferably a Java application (JDK Ver. 1.1 or JRE) running on a supported UNIX platform (e.g., Linux, Irix, Solaris). The Database Server is preferably SQL-capable (e.g., MYSQL, Oracle). The Application Server and Database Server communicate via the protocol implied by the JDBC (Java Database Connectivity) driver of the RDBMS. The Application Server preferably completely isolates the client from any notion of relational databases; the client's view is one of (Java) objects, not relations.

The present invention also envisions other computing arrangements for the client and server(s), including processing on a single machine such as a mainframe, a collection of machines, or other suitable means.

IV. Client/Server Communications

The client and server machines work together to accomplish the processing of the present invention. The preferable protocol between the client and server is RMI (Remote Method Invocation for Java-to-Java communications across Virtual Machines). RMI is a standard defined by the Java Core.

Figure 3:
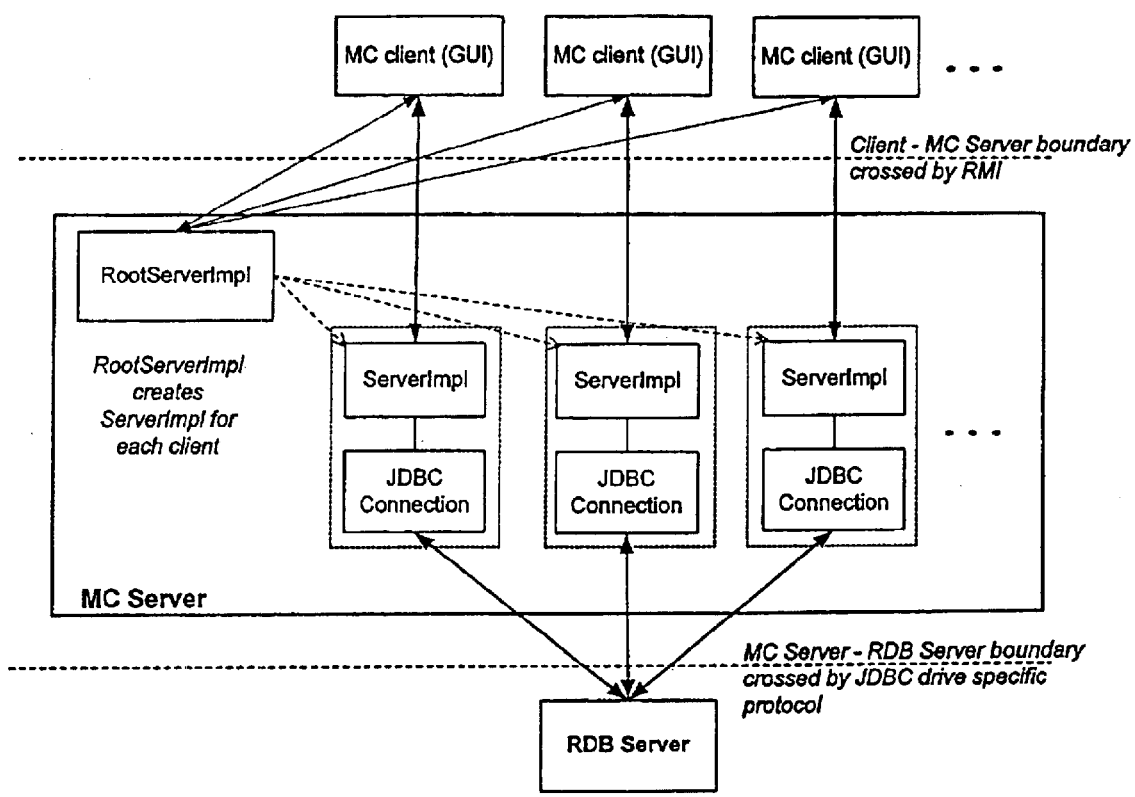
FIG. 3 depicts the preferred client/server communication model with all three tiers.

The isolation of clients from each other requires that each client gets its own server instance as a container of all client related data like database connection or query status. A root server allows connection bootstrapping by creating server instances. The resulting communication model with all three tiers is depicted in FIG. 3.

V. Database Hardware

The database is preferably connected to the database server component and can be any device which will hold data. For example, the database can consist of any type of magnetic or optical storing device for a computer (e.g., CDROM, internal hard drive, tape drive). The database can be located remote to the server component (with access via modem or leased line) or locally to the server component.

VI. Database Type (Relational)

The database is preferably a relational database created/derived from existing biological data sets and/or databases (e.g., SwissProt, GeneBank) that is organized and accessed according to relationships between data items. In a preferred embodiment, the database is SQL compatible with standard JDBC supported mechanisms and datatypes. The relational database would preferably consist of a plurality tables (entities). The rows of a table represent records (collections of information about separate items) and the columns represent fields (particular attributes of a record). In its simplest conception, the relational database is a collection of data entries that "relate" to each other through at least one common field.

VII. Database Tables

Figure 4A:
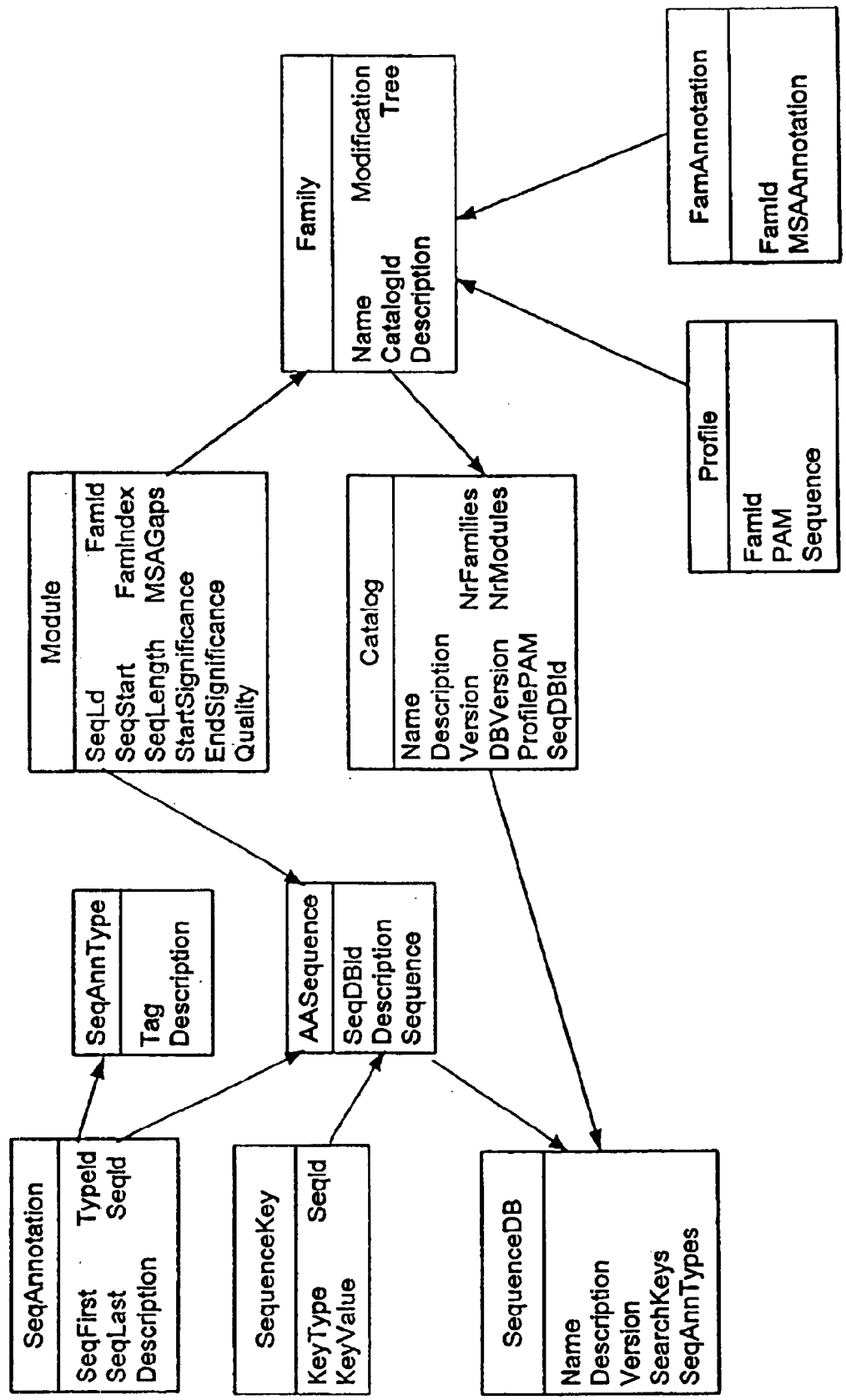
FIG. 4A depicts the entity relationship diagram of one embodiment of the database.
Figure 4B:
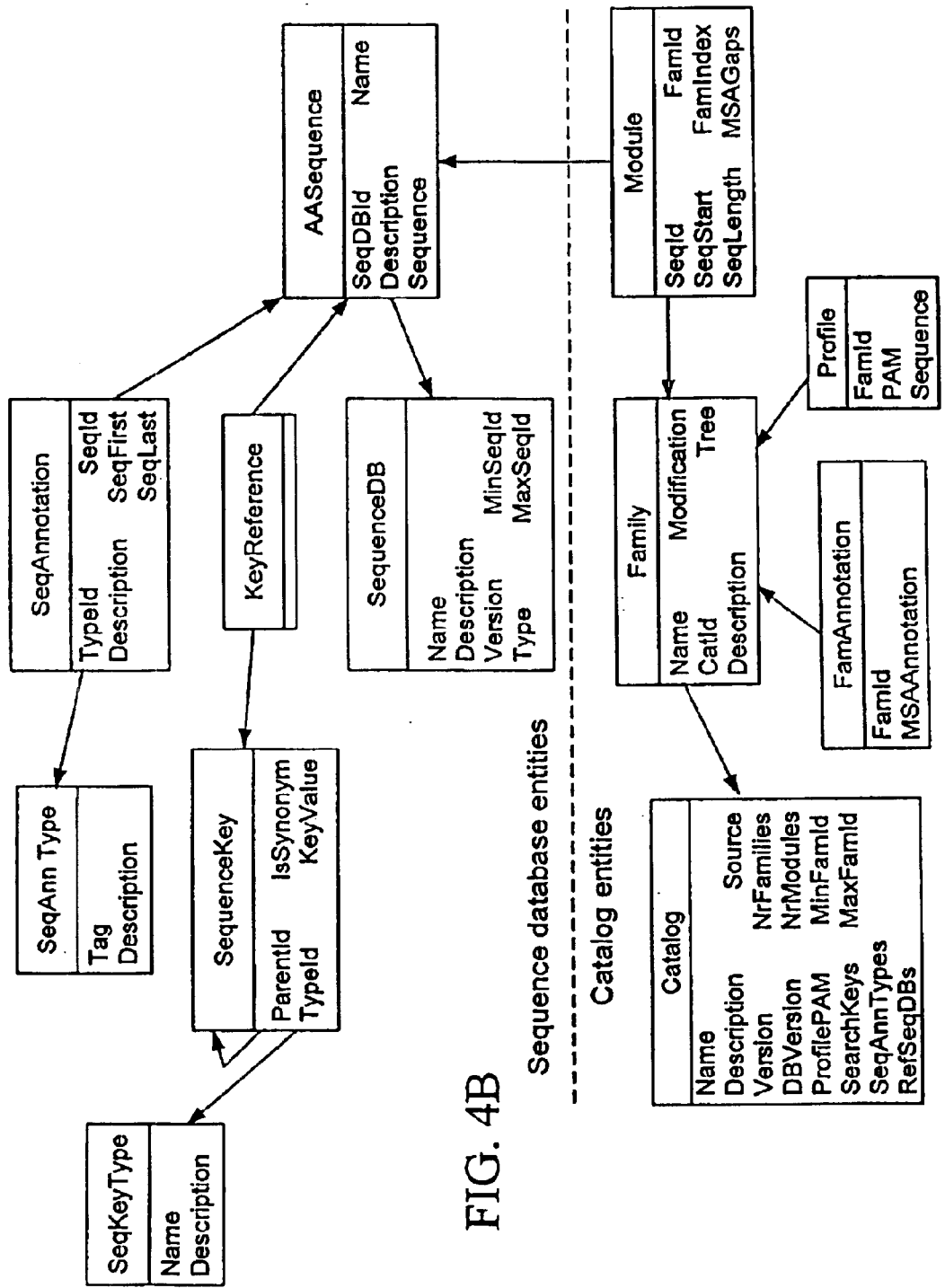
FIG. 4B depicts the entity relationship diagram of another embodiment of the database.
Figure 4C:
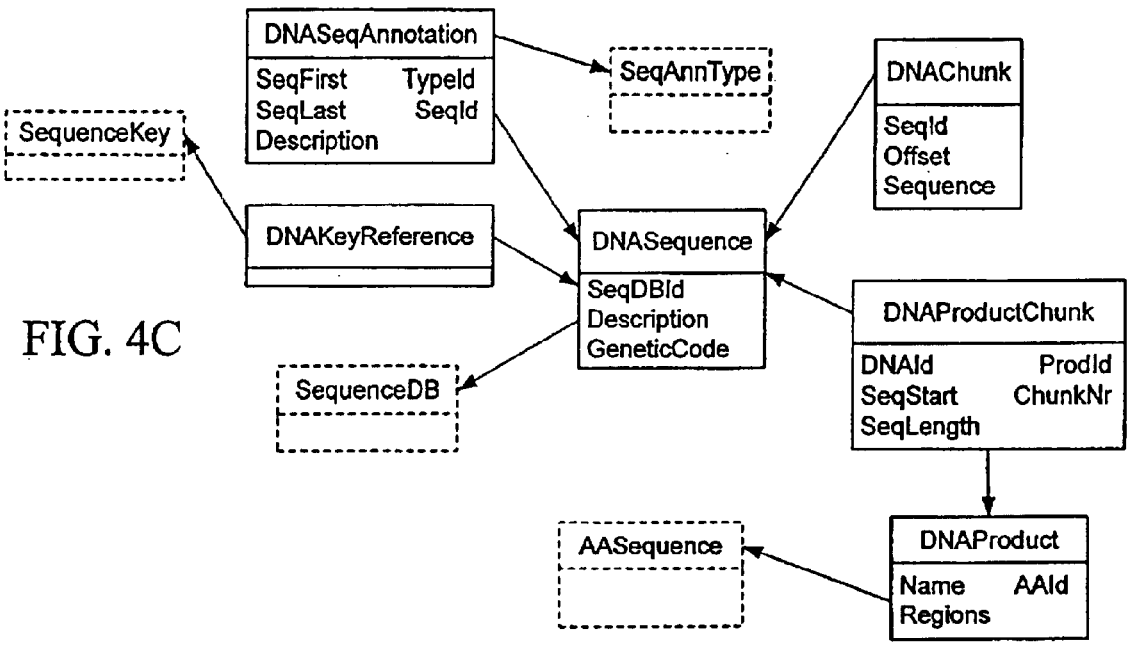
FIG. 4C depicts the entity relationship diagram for DNA.
Figure 5:
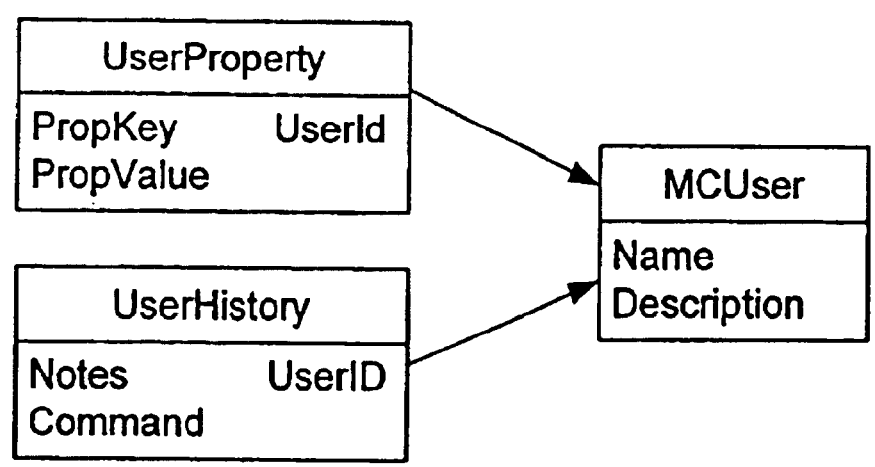
FIG. 5 depicts the block diagram for user related database.

Each separate table (entity) represents a difference schema of interconnections between some or all of the protein sequences from the underlying biological data set/database. Three versions of this schema can be viewed using the entity relationship diagrams of FIGS. 4A–4C which illustrates the fields for each type of data and the interconnections between data types. The following is a detailed description of a collection of tables (entities) in one embodiment of the present invention with the attributes and keys of each relation. The ID field of all relations except those of the SeqAnnType table is assigned automatically when inserting the relation. In particular, FIG. 4C shows the entity relationship diagram for DNA.

1. AASequence Table

The AASequence table contains all amino acid sequences available in the database. Every sequence belongs to exactly one sequence database.

| # | Name | Type | Key | Description |
|---|---|---|---|---|
| 1 | Id | INTEGER | P | The internal id, i.e. the foreign key for all modules, sequence annotations and sequence keys belonging to this sequence. |
| 2 | SeqDBId | INTEGER | | The sequence database the sequence belongs to. |
| 3 | Description | VARCHAR (255) | | A description of the sequence. |
| 4 | Sequence | LONGVARCHAR | | The sequence itself as encoded characters according to Alphabet.getAminoAcidAlphabet ( ). |

2. Catalog Table

The Catalog table contains all catalogs available in this database.

| # | Name | Type | Key | Description |
|---|---|---|---|---|
| 1 | Id | INTEGER | P | The internal id, i.e. the foreign key for all families belonging to this catalog. |
| 2 | Name | VARCHAR (64) | S | The unique name for external identification. |
| 3 | Description | VARCHAR (255) | | A description of the catalog's contents. |
| 4 | Version | VARCHAR (16) | | The version of this catalog (a date or a version according to some numbering scheme). |
| 5 | DBVersion | INTEGER | | The database format version of this catalog. The format version is used to verify the compatibility of database and MC server. |
| 6 | ProfilePAM | float [ ] | | The list of PAM of the available profile databases. It caches the result of a time consuming query. |

-continued

| # | Name | Type | Key | Description |
|---|---|---|---|---|
| 7 | NrModules | INTEGER | | The total number of modules in this catalog. It caches the result of a time consuming query. |
| 8 | NrFamilies | INTEGER | | The total number of families in this catalog. It caches the result of a time consuming query. |

3. FamAnnotation Table

The FamAnnotation table contains all annotations of all families. An annotation always belongs to exactly one family.

| # | Name | Type | Key | Description |
|---|---|---|---|---|
| 1 | Id | INTEGER | P | The internal id. |
| 2 | FamId | INTEGER | F | Foreign key to the corresponding family. |
| 3 | Annotation | ds. MSAAnnotation | | The annotation of the MSA of the family. |

4. Family Table

The Family table contains all families of all catalogs. A family always belongs to exactly one catalog and contains an arbitrary number of modules.

| # | Name | Type | Key | Description |
|---|---|---|---|---|
| 1 | Id | INTEGER | P | The internal id, i.e. the foreign key for all modules, profiles and MSA annotations belonging to this family. |
| 2 | Name | VARCHAR (64) | S | The name of this family assigned during modularization. |
| 3 | Modification | INTEGER | S | The modification number of this family inside its once assigned name. |
| 4 | CatId | INTEGER | | Foreign key to the containing catalog. |
| 5 | Description | VARCHAR (255) | | The description of this family (usually generated automatically during modularization). |
| 6 | Tree | ds. Tree | | The precalculated phylogenetic tree of this family. |

5. Module Table

The Module table contains all modules of all catalogs. A module always belongs to exactly one sequence and exactly one family. The multiple sequence alignment is implicitly stored as a Gaps structure from which the MSA can be directly constructed.

| # | Name | Type | Key | Description |
|---|---|---|---|---|
| 1 | Id | INTEGER | P | The internal id. |
| 2 | SeqId | INTEGER | F | Foreign key to the containing sequence. |
| 3 | Seqstart | INTEGER | | Start of this module in the containing sequence (o based). |
| 4 | SeqLength | INTEGER | | Length of this module in the containing sequence. |
| 5 | FamId | INTEGER | F | Foreign key to the containing family. |
| 6 | FamIndex | INTEGER | | Index of this module in the containing family. |
| 7 | Start-Significance | REAL | | Significance of start point of this module. |
| 8 | End-Significance | REAL | | Significance of end point of this module. |
| 9 | Quality | REAL | | Overall quality of this module. |
| 10 | MSAGaps | ds. Gaps | | Gaps to be inserted in this module's sequence to obtain the MSA sequence. |

6. Profile Table

The Profile table contains all profiles of all families. A profile always belongs to exactly one family. For each family, there may be several profiles at different PAM.

| # | Name | Type | Key | Description |
|---|---|---|---|---|
| 1 | Id | INTEGER | P | The internal id. |
| 2 | FamId | INTEGER | F | Foreign key to corresponding family. |
| 3 | Pam | REAL | S | PAM distance from the PAS of the family. |
| 4 | Sequence | BLOB | | The actual profile sequence in packed representation (byte [ ]). |

7. SeqAnnotation Table

The SeqAnnotation table contains all annotations of all sequences in this database. Each annotation belongs to exactly one sequence.

| # | Name | Type | Key | Description |
|---|---|---|---|---|
| 1 | Id | INTEGER | P | The internal id. |
| 2 | SeqId | INTEGER | F | Foreign key to the containing sequence. |
| 3 | SeqStart | INTEGER | | Start of this annotation in the containing sequence (0 based). |
| 4 | SeqLength | INTEGER | | Length of this annotation in the containing sequence. |
| 5 | Type | INTEGER | F | The sequence annotation type as defined by SeqAnnType. |
| 6 | Description | VARCHAR (255) | | A description of the annotation in addition to the one provided by SeqAnnType. It may be missing, i.e. NULL. |

8. SeqAnnType Table

The SeqAnnType table contains all types of all sequence annotations in this database. Its main purpose is to provide standard descriptions for each type to be displayed in the GUI. This entity has more the character of a lookup table than of a real database entity. The Id attribute of each relation is assigned manually. The semantics of some IDs must be known to e.g. the GUI, as different annotations will be displayed differently. Types are collected into groups (type id ranges) whose members normally do not overlap (e.g. secondary structure or binding sites). The groups are predefined in mastercatalog.ds.SeqAnnGroup.

| # | Name | Type | Key | Description |
|---|---|---|---|---|
| 1 | Id | INTEGER | P | The internal id. |
| 2 | Tag | VARCHAR (32) | S | The tag used in the original annotation database corresponding to this type (e.g. a feature table tag). |
| 3 | Description | VARCHAR (255) | | A description of the annotation. |

9. SequenceDB Table

The SequenceDB table contains all sequence databases available in this database.

| # | Name | Type | Key | Description |
|---|---|---|---|---|
| 1 | Id | INTEGER | P | The internal id, i.e. the foreign key for all sequences belonging to this database and all catalogs built from this database. |
| 2 | Name | VARCHAR (64) | S | The unique name for external identification. |
| 3 | Description | VARCHAR (255) | | A description of the database contents. |
| 4 | Version | VARCHAR (16) | | The version of this database (a date or a version according to numbering scheme). |
| 5 | SearchKeys | String [ ] | | The list of available search keys for sequence searches. It caches the result of a time consuming query. |
| 6 | SeqAnnTypes | String [ ] | | The list of available sequence annotations. It caches the result of a time consuming query. |

10. SequenceKey Table

The SequenceKey table contains all indexed keys of a sequence like ID, accession numbers, EC numbers and so on. Storing these keys separately allows additional key types to be added without modifying the database structure or any code. Furthermore, there may be multiple occurrences of the same key type for any sequence.

| # | Name | Type | Key | Description |
|---|---|---|---|---|
| 1 | Id | INTEGER | P | The internal id. |
| 2 | KeyType | VARCHAR (16) | | The key type, e.g. "EC". |
| 3 | KeyValue | VARCHAR (255) | S | The key value, e.g. "4.2.1.1". |
| 4 | SeqId | INTEGER | F | Foreign key to corresponding sequence. |

Short arrays and graphs are preferably stored as BLOBs (Binary Large Objects) to prevent uncontrolled growth of the number of entities in the design. Only large arrays of variable size are stored in their own relation by properly normalizing the database. The mapping between transient Java objects and persistent database relations (rows in a DB table) is based on a unique "Id" (an INTEGER) for each relation. References to other objects in the database are therefore always INTEGER foreign keys.

For each table, there is a subclass whose instances are Java objects corresponding to relations, and a subclass representing the corresponding entity and providing the necessary SQL code.

VIII. GUI

The operation of the present invention will now be described with respect to the graphical user interface and its navigation of the database.

The graphical user interface of the present invention allows the user to browse the sequence database, perform searches, and examine evolutionary relationships. For example, the GUI is a browser that can be used to follow evolutionary relationships through the genomic sequence; the browsing provides interactive trees, multiple sequence alignments, and families; the database of families can be searched using a novel method that represents each family as a probabilistic sequence; rates of evolution are displayed on evolutionary trees and provide evidence of changes in function.

As in most "windows" applications, each display screen of the invention generally comprise a window title bar, a menu bar (with command such as File, Edit, and the like), a tool bar (with options such as Close, Paste, Clear, and the like), and an information display region. The information display region may, for example, display a query window or a results window.

Figure 6:
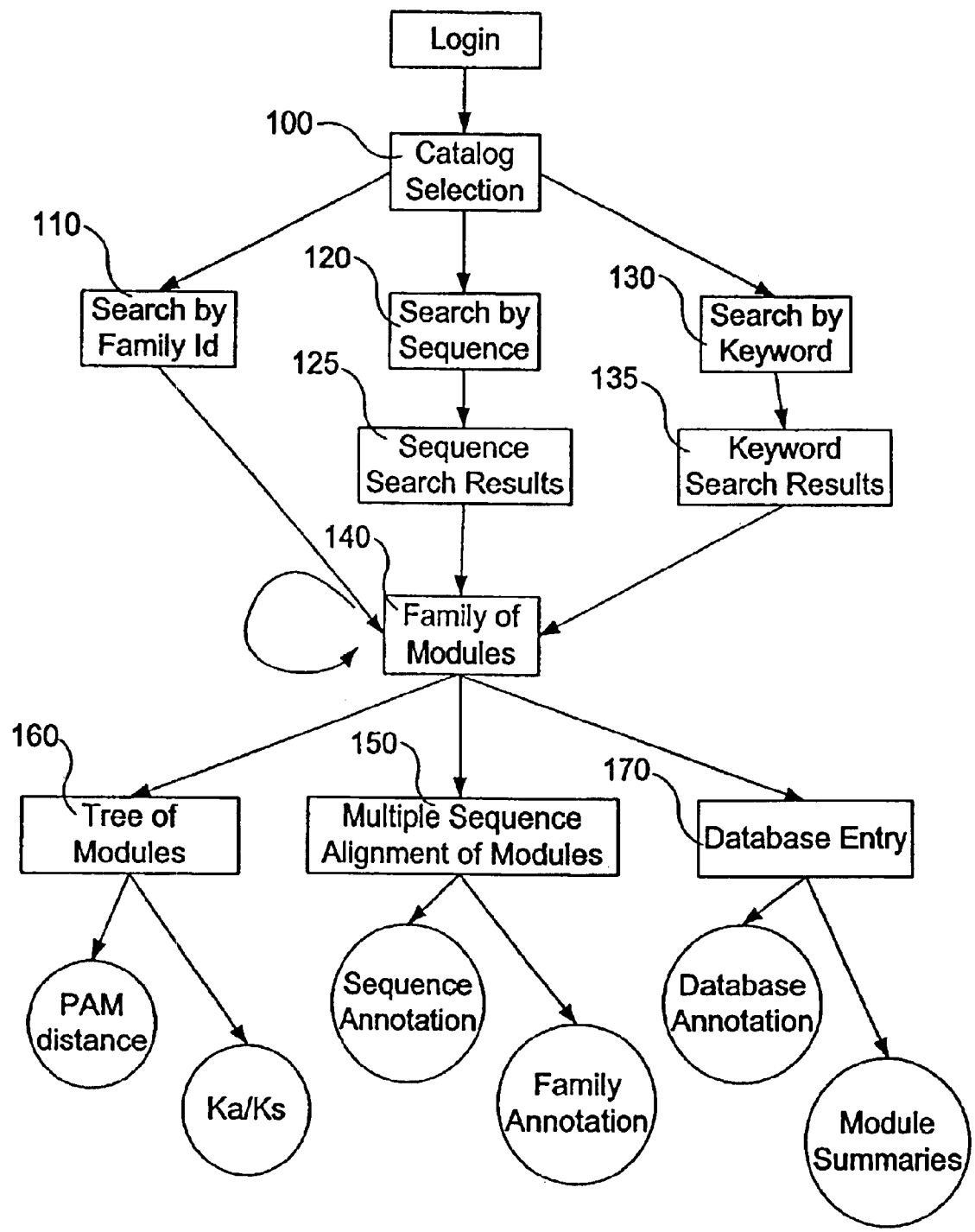
FIG. 6 is a navigational flowchart of a preferred embodiment of the invention illustrating all major windows and options available.

FIG. 6 is a navigational flowchart of a preferred embodiment of the invention illustrating all major windows and options available. Rectangles represent the windows and circles represent options available within their respective windows. Arrows indicate direction [and each layer of the program is color coded].

Preferably, the initial window is a LOGIN window (not shown) wherein a user may enter a valid user name and password to access the system.

Upon a successful login, the CATALOG SELECTION WINDOW 100 appears in the user's display as shown in a pictorial diagram in FIG. 7 according to an embodiment of the invention. The CATALOG SELECTION WINDOW 100 displays the available catalogs for selection by name, version, description, number of families and number of modules.

Each catalog is constructed to provide a view of relationships between (some or all of) the protein sequences in the database. Different catalogs emphasize different features of the protein sequence database. For example, one catalog might emphasize repeat units within proteins, another catalog focuses on alignments which comprise the whole length of genes (e.g., a gene product catalog), and another focuses on local patterns of divergence between protein sequences (e.g., a modularized catalog). Catalogs are composed of families of modules, each module defining a region of a protein sequence. Thus, the families relate regions of different protein sequences in biologically meaningful ways.

In the database configuration, the Catalog table (described previously) contains the following: Id, Name, Description, Source, Version, DBVersion, ProfilePAM, NrModules, NRFamilies, MinFamId, MaxFamId, SearchKeys, SeqAnnTypes, RefSeqDBs.

Examples of catalogs which may be included in the present invention include the following:

1. Modularized catalog: A description of relationships between protein sequences based on local patterns of divergence (according to a model of evolution). There are many ways in which such a catalog might be constructed. Published examples include ProDom and DOMO.

2. Gene product catalog: A description between protein sequences one or more of which must comprise whole genes. Example of a method for building a catalog of this type can be seen in Monica Riley's work on Modularization of the *E.coli* genome.

3. Repeat catalog: A description between regions of proteins which form identifiable repeats of at least 20 residues. Certain features of the DOMO database show features of this type, although this database is more properly defined as a modularized catalog.

4. Entry catalog: A description defining the 'classical' method of sequence database construction. That is that there are no explicit relationships between different sequence entries. It is simply a dictionary of all available protein sequences in the database.

Catalogs can be subsets of all data in the database. Typically this is most (scientifically) useful for the modularized catalogs where focusing on a subset of all the gene products (e.g. just mammalian sequences) is biologically meaningful (e.g., mammalian modularized catalog, bacterial modularized catalog).

Selecting a catalog by double clicking on one of the available catalogs displays a query window for that catalog. Alternatively, you can select a catalog entry with the mouse and click on the Open button on the toolbar.

There is a special catalog, 'the Sequence Entry Catalog' that contains just the individual protein sequences. This catalog necessarily does not have family names or allow sequence searching; it merely provides direct access to individual protein sequences and can be searched by keyword.

Once a catalog is chosen, there are several different ways to search the catalog: a) by catalog family identifier, b) by keyword, and c) by sequence. In a preferred embodiment, the query type is selected using "tabs" associated with each search type. Each search method yields unique results providing a rich mechanism for navigation to related modules. All of these methods may not be available for every catalog (i.e., if there is no family, there would be no family identifier). The methods are described in more detail hereafter.

a). FIG. 8—Search by Name (Family identifier/Module ID): Each family in a catalog preferably has a unique identifier that defines a particular family. Preferably, these family names are generated automatically when each catalog is built from the protein sequence data. This search window 110 allows you to obtain a specific family number of interest as shown in FIG. 8. The result of this search is the Module Family Summary (MFS)window 140 of FIG. 9 showing a graphical view of the associated proteins and their modules.

b). FIG. 10—Search by Sequence: This window 120 allows you to search a protein against a catalog for homologous (evolutionarily related) protein families as shown in FIG. 10. Homology is an important concept in extracting information from sequence databases because conclusions can be drawn about the chemical behavior and biological function when two proteins are homologous. One way to determine whether two proteins are homologous is to compare their amino acid sequences. Procedures are well established in the art for comparing two protein sequences, scoring similarities, and using this score to assess the likelihood that the similarities arose by reason of common ancestry rather than by random chance [Gonnet, G. H., Cohen, M. S., Benner, S. A. Exhaustive matching of the entire protein sequence database. Science 256, 1443–1445 (1992)]. You can enter the amino acid of interest, specify a minimum scope and maximum amount of matches, and adjust the PAM sensitivity. (The sensitivity of the search can be set, for example, at 50 PAM to look for close homologs of 150 PAM to detect long distance homology. Only the hits above the specified minimum score and up to the maximum amount of matches are reported). This search can take awhile for large probe sequences. You can abort the search at any time with the cancel button.

The result of this search is a Sequence Search Results (SSR) window 125 showing a graphical view of the relationship between the probe sequence and the associated families as shown in FIG. 11. This window shows the relationship between the probe sequence chosen for the query and each of the families that are related. The score corresponds to a 'log odds score', the probability that the relationship between the sequence is related according to the model of evolution vs. the probability that the similarity is by chance.

Double clicking on any module shown in SSR window will display the module family summary (MFS) window 140 for that family. The alignment of the probe sequence with the summary can then be displayed.

c). FIG. 12—Search by Keyword: This window 130 provides searches of the protein sequence database by keyword, according to annotations of proteins in the original sequence database as shown in FIG. 12. Keywords provided include selection by organism, by classification, by gene name and by gene product description.

The result of this search is a keyword search results (KSR) window 135, FIG. 13, includes a list of database sequence ID's which have database sequence annotations matching the keywords in the description. The display shows a graphical view of the individual protein sequences which fit the keyword search criteria. The graphical view is shown as a linear arrangement of schematic boxes (spatially oriented) representing the existing modules found in the selected catalog along the identified amino acid range (AA). Each of the schematic boxes is preferably identified with its corresponding Module ID number and is differentiated by color or another form of distinctive representation. In some cases, sequences may match with a particular keyword but no modularization information is available (and no schematic boxes shown) because these sequences were not part of the set included in the currently selected catalog.

Double clicking on any module shown in the KSR window 135 will display the module family summary (MFS) window 140 for the associated family.

The Module Family Summary (MFS)window 140 of FIG. 9 showing a graphical view of the associated proteins and their modules will now be described in detail. This window is the gateway to navigational power of the present invention by providing a gateway to other displays. The window shows all of the sequences in the currently selected catalog that are members of a particular family, where the family contains all of the sequences which have a particular module of interest. All relationships between modules have been precalculated in the database. The module is a subsequence that is a member of family where the graphical length is proportionate. Unidentified regions do not have schematic boxes. The module of interest is preferably visibly distinguished from the other modules and its ID is identified in the title bar of the window. The sequences in the family may also contain other modules. The sequences are ordered to cluster modules which are closest together in evolutionary distance.

The window is preferably tabular with a separate numbered row for each sequence. The columns preferably include the sequence ID, a description, the amino acid range and a graphical view of the sequence shown as a linear arrangement of schematic boxes (spatially oriented) representing the existing modules found in the selected catalog along the identified amino acid range (AA). Each of the schematic boxes is preferably identified with its corresponding Module ID number and is differentiated by color or another form of distinctive representation. The schematic boxes for the currently selected module are vertically aligned and visually distinguished, such as by color (red). The windows "tool tips" feature may expand any truncated descriptions or provide additional information in a floating window when the pointer is placed over a particular table entry. This window provides a good indication of any long distance homology between various modules. Proteins that share a common module frequently possess other homologous modules at analogous positions. Such relationships can be confirmed by examining multiple sequence alignments and trees.

The toolbar of the MFS window allows you to perform many different tasks from this point (e.g., print, export to disk, display multiple sequence alignment (MSA), and display phylogenetic tree). Each of these tasks will now be discussed in detail. The family summary can be printed directly to a printer available from a local computer. The description of the modularization of this family can be exported to file.

Figure 14A:
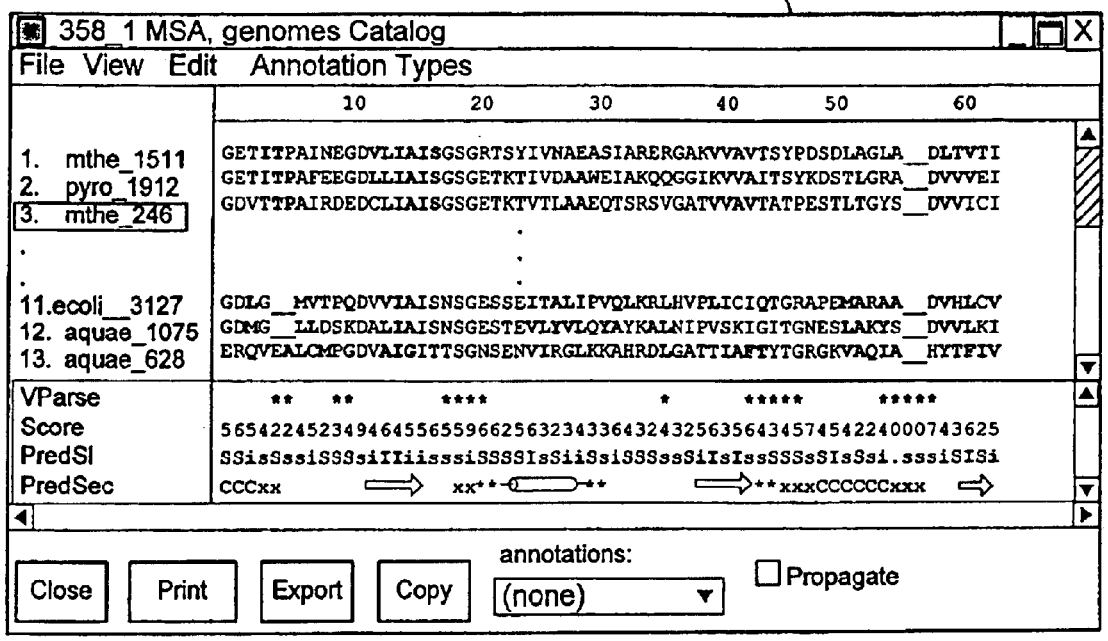
FIG. 14 depicts a sample screen display for the MSA window.
Figure 14B:
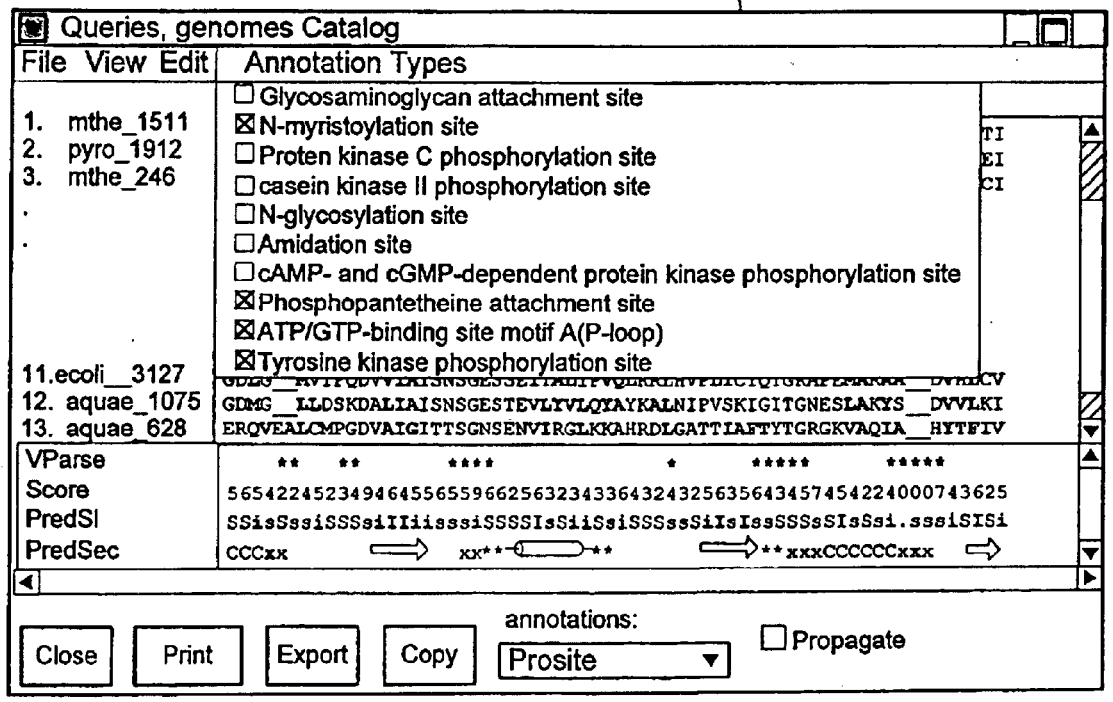

We now turn to FIG. 14 for the display of the multiple sequence alignment (MSA) of the current family. Selecting the MSA button on the window's toolbar shows the multiple sequence alignment (the way in which the modules are related at the amino acid level) in the MSA window 150 of FIG. 14. This window provides detailed evolutionary information at the protein sequence level to following pattern of conservation and variation of amino acid composition of the module. The MSA is preferably colored according to hydrophobic or hydrophilic nature of the amino acids. (e.g., RED indicates hydrophobic propensity and BLUE indicates hydrophilic). The numbering system uses in the MSA window preferably corresponds to the number system implemented by both the MFS window and the Tree window. Highlighted on each sequence are annotated regions of individual protein sequences. Moving the cursor (pointer) over a chosen highlighted region displays the annotations in a floating window. These can be hand-crafted comments, such as feature table entries from SWISS-PROT or automatically generated from patterns such as those in PROSITE (or others such as PRINTS). Different annotations can be selected from the option bar at the bottom of the MSA window.

Analyzing correlations in the patterns of substitution in the sequences for each module family allows predictions to be made about the nature of underlying structural or functional constraints. Preferably, the annotations provided are Vparse, showing the location of putative structure breaking residues or motifs and Score, showing the degree of conservation at each position in the alignment. This value is dependent on both the evolutionary distances between the sequences and the mutability of the individual amino acids, and is a sensitive indicator of significance of conserved sites; PredSI, indicating the predicted solvent accessibility of the residue at that position; and PredSec, indicating the predicted secondary structure. If the PAM width of the family is poor or the number of sequences is small, then there may be insufficient information for a secondary structure prediction. If the given module aligns significantly with any entry in the PDB indicating a confident homology, a string of secondary structural elements corresponding to that alignment can be seen at the bottom of the MSA window below PredSI and PredSec strings.

As previously described, the multiple sequence alignment window shows the amino-acid by amino-acid relationship between proteins which are in the same family. Some preferred features include a) Coloring: Hydrophobic residues in red, hydrophilic residues in blue, amphiphilic residues in black, b) Parses: Regions of sequence which are likely to represent secondary structure breaking positions, are indicated, c) PredSI: Predicted surface/interior residues are indicated, d) PredSec: Predicted secondary structure is shown, e) Experimental Sec: If known, the secondary structure of experimentally determined homologs to the family are shown, f) Annotation: Sequence features, such as motifs of well known function can be selected from the 'annotations:' list box in the window (see below). Functions of the MSA window include: a) Export sequence data: The sequence of selected modules of this family can be exported to file in a variety of formats, b)Copy sequence data to clipboard: The sequence of selected modules of this family is copied to the clipboard when this button is selected, c) Print: The family summary can be printed directly to any printer available from your local computer, d) Annotations: The sequences in the MSA can be highlighted for particular annotations (usually specific sequence motifs or special database annotations). One such collection of annotations is the 'Prosite' database. Regions of sequence corresponding to Prosite annotations are colored in orange. Moving the cursor over that region of the text displays the details of the annotation in a floating window. The complete set of annotations visible in the current window can be obtained by looking at the 'Annotation Types' menu. A subset of all the annotations in the current collection can be obtained by customizing with the tickboxes in the annotation menu.

Selection of sequences/modules will now be described. You can select some or all of the sequences of individual modules. Sequences are selected individually in the MSA display with single mouse clicks. To combine your selection with previous selections, keep the <CTRL> key depressed while selecting. In addition to the toolbar tasks, other features are available from the window. For example, double clicking on any sequence in the ID column shows the protein sequence window for that family (including catalog membership, description, and annotations).

Figure 15A:
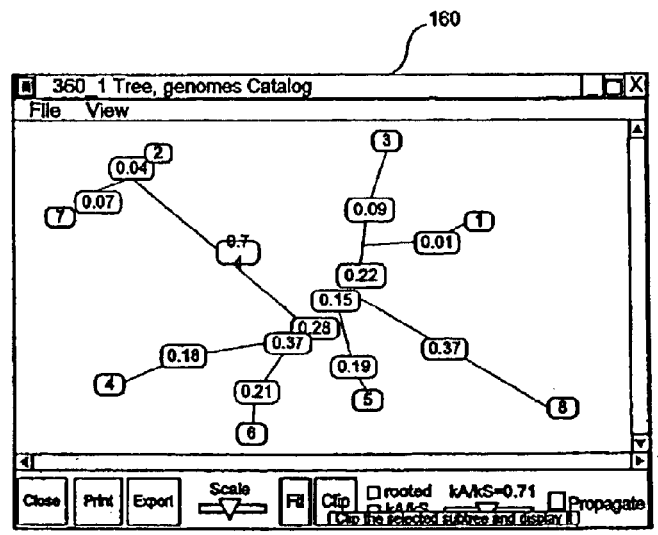
FIG. 15 depicts a sample screen display for the evolutionary tree window.
Figure 15B:
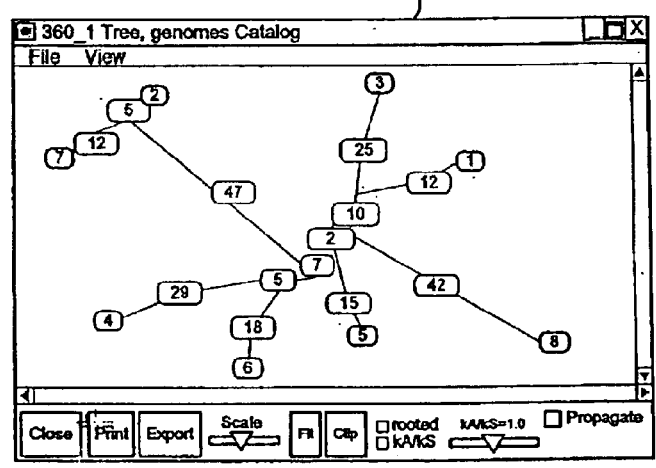
Figure 15C:
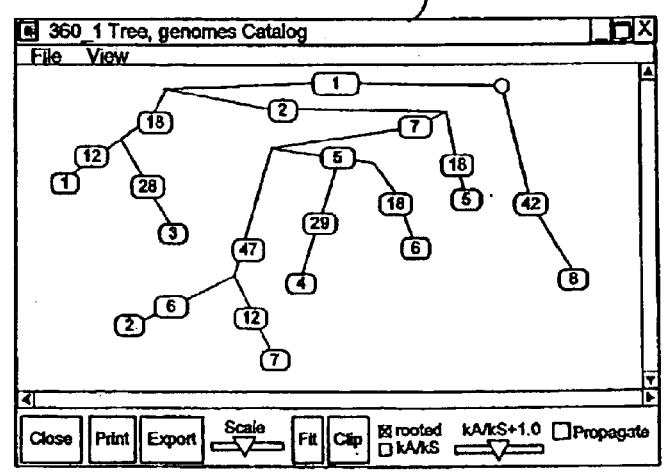

We now turn to FIG. 15 for the display of the evolutionary tree of the current family. Selecting the Tree button on the MFS window shows the evolutionary tree in the Tree window 160 of FIG. 15. This indicates the pattern of divergence/similarity between individual modules, assuming that the distance between modules can be computed from the similarity in the protein sequences. Specifically, trees show an estimate of the evolutionary history of a protein module, constructed using the PAM distances between individual members of that family. Trees may be displayed either as rooted or unrooted form; there is no significant distinction between these representations, the location of the root being chosen to balance the tree.

On the branches of the tree, the length of the branches are displayed in PAM units. This provides an estimate of divergence in composition of the various sequences. Selecting the "kA/kS" key at the bottom of the window will display the ratio of the rate of expressed changes at the DNA level to the rate of silent changes, i.e., the rate of mutation leading to changes at the protein level calibrated against the rate of mutation leading to changes only at the DNA level.

The rates are preferably normalized so that when reading expressed:silent ratios, a value of around 1.0 indicates no selection, both synonymous (silent changes) and non-synonymous (expressed changes) substitutions being equally likely (e.g., a pseudogene). The threshold level of kA/kS is user adjustable on the slide scale. Separate coloring schemes are preferably used to indicate branches above or below the threshold. For example, if kA/kS is less than the threshold (default 1.0) the branch is colored blue and if kA/kS is greater than the threshold, the branch is colored red. If no DNA sequence information is available, then the branch is colored black. In practice, proteins are normally under the influence of purifying selection so the ratios fall well below this value. Therefore, where the ratio approaches or exceeds 1.0, the confidence that one is looking at an episode of rapid sequence evolution (presumably to new function) increases. For adaptations which occurred at longer evolutionary times, the value of the expressed:silent ratio will appear lower as random mutation has increased the number of silent changes. A suitable threshold value can be determined by examining the tree as a whole, which will contain branches that have maintained purifying selection for longer periods and comparing these values with those that suggest mere rapid changes at expressed sites.

The graphic interface also offers scaling facility to zoom in and zoom out using the slide scale at the bottom of the window. Zooming may be necessary in order to see the PAM distance labels or leaf identifiers. This information can also be seen in a floating window by positioning the cursor over the leaves or branches. Individual branches can be displayed on separate trees by selecting the appropriate branches and the "Zoom" key. The "fit" button sizes the tree to the full window size.

As previously described, the Tree window shows the evolutionary relationship between individual modules of a family, using distance calculated from a comparison of their amino acid sequences. Some preferred features include: a) Coloring: Blue edge—KaKs (see below) below threshold, Red edge—KaKs above threshold, Black edge—KaKs not computed (no DNA/unreliable DNA sequence). The threshold is selected by changing a slide bar on the toolbar of the Tree window, b) Rooted/Unrooted: The tree can be displayed in rooted, or in unrooted form, depending on user preference. There is no difference in information content between these two descriptions; the root of the tree is chosen for balance, not as a result of other phylogenetic evidence. Some preferred function include: a) Export tree description: The tree can be exported to file in a variety of formats, b) Print: The tree can be printed directly to any printer available from your local computer, c) Annotations: The sequences in the MSA can be highlighted for particular annotations (usually specific sequence motifs or special database annotations). One such collection of annotations is the 'Prosite' database. Regions of sequence corresponding to Prosite annotations are colored in orange. Moving the cursor over that region of the text displays the details of the annotation in a floating window. The complete set of annotations visible in the current window can be obtained by looking at the 'Annotation Types' menu. A subset of all the annotations in the current collection can be obtained by customizing with the tickboxes in the annotation menu; d) Selection sequences/modules: You can select branches or leaves of the tree with single clicks of the mouse. Selecting a branch will result in all of the branches and leaves being selected downstream of the root. (The root is marked with a circle). To combine your selection with previous selections, keep the <CTRL> key depressed while selecting; e) Fit tree/Rescale tree: The fit button can be used to rescale the tree to fit into the entire window. Pressing SHIFT and the left mouse button can be used to zoom in toward the selected portion of the window, and SHIFT with the right mouse button will zoom out from the selected portion of the window; f) Ka/Ks: You can display either KaKs or PAM distances on the tree.

The MFS window, tree window and MSA window are linked so that selections in one window highlight sequences in the other. You can select some or all of the modules possessed by individual sequences. Modules are selected individually in the MFS window with single mouse clicks. All of the modules possessed by a protein can be selected at once by selecting the module id (#) on the left hand column. To combine your selection with previous selections, keep the <CTRL> key depressed while selecting.

Normally selections propagate through displays of the current family, i.e., selecting sequences in any window that applies to a family highlights that module in every display for that family—the Tree window, the MSA window and the MFS window. If the propagate check box is set, selections propagate by sequence—i.e., all proteins sequences possessing any selected modules are highlighted. This mode is extremely useful when tracing relationships across different protein families.

We will now describe navigation to another family (related by membership with sequences in the current family). Double clicking on any module in the graphical representation displays the family summary window corresponding to that module.

Notable features of the present invention include a) multi-catalog views where a user can simultaneously view more then one catalog, b) tree to tree interactivity where active selections from a current window get propagated throughout (selected and deleted), c) connectivity of selections where a section of a tree as selected will highlight associated information in other windows which is continuously applied as windows are opened, d) the MSA window's Prosite annotations, tool tips to show annotations, and customization of annotation display/view to select subsets.

Following are examples which illustrate procedures for practicing the invention. These examples should not be construed as limiting.

EXAMPLE 1

FIG. 16 depicts an example of consecutive screen displays for interactive and progressive query-making activity from search by sequence. First a sequence is typed or cut and pasted into the query box 120. Minimum scope, maximum matches and PAM are adjusted by the user as desired. The query is then run resulting in the Sequence Search Results (SSR) window 125. From this window, the user can progressively query the desired module(s) by double-clicking on that module(s) which results in the MFS window 140 with the module of interest designated in RED and positionally aligned with all other modules.

EXAMPLE 2

Figure 17:
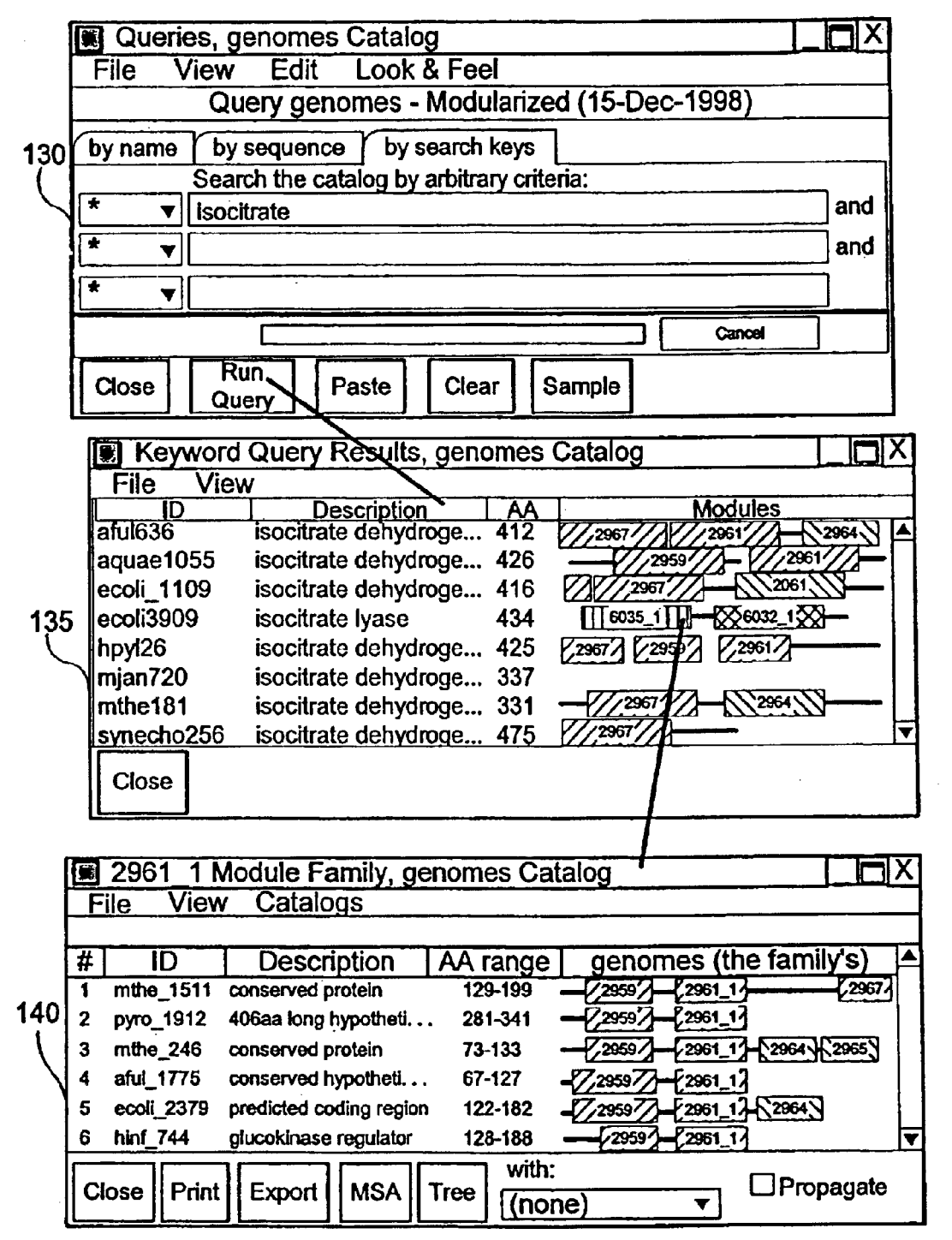

FIG. 17 depicts an example of consecutive screen displays for interactive and progressive query-making activity from search by keyword. The search term "isocitrate" is entered (other search terms may be included with the necessary boolean logic) in the query window 130. After the query is run, the Keyword Search Results (KSR) window 135 is displayed listing all sequences which contain the queried keyword with the graphical display of the sequences and their modules. From this window, the user may select a module of interest to be displayed in the MFS window 140. The MFS window 140 shows the two-dimensional spatial orientation of the biological data, including visual locations of modules (represented as schematic boxes) in each of the sequences for a selected family distinguishably displayed and positionally aligned as well as the location of all other modules in those sequences.

EXAMPLE 3

Figure 18A:
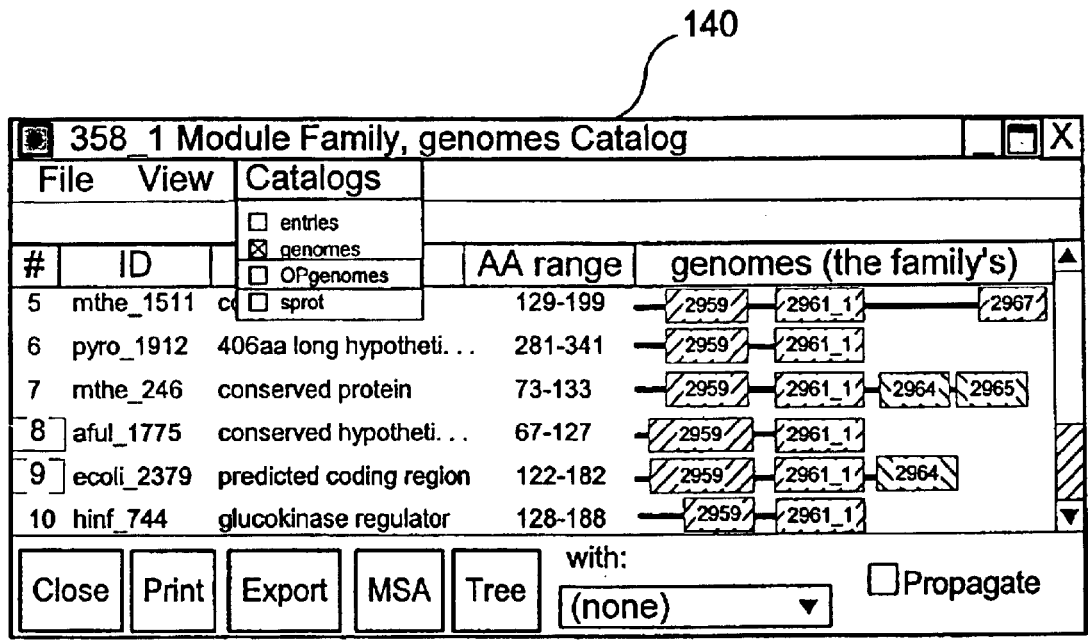
FIG. 18A depicts the MFS window for one catalog.
Figure 18B:
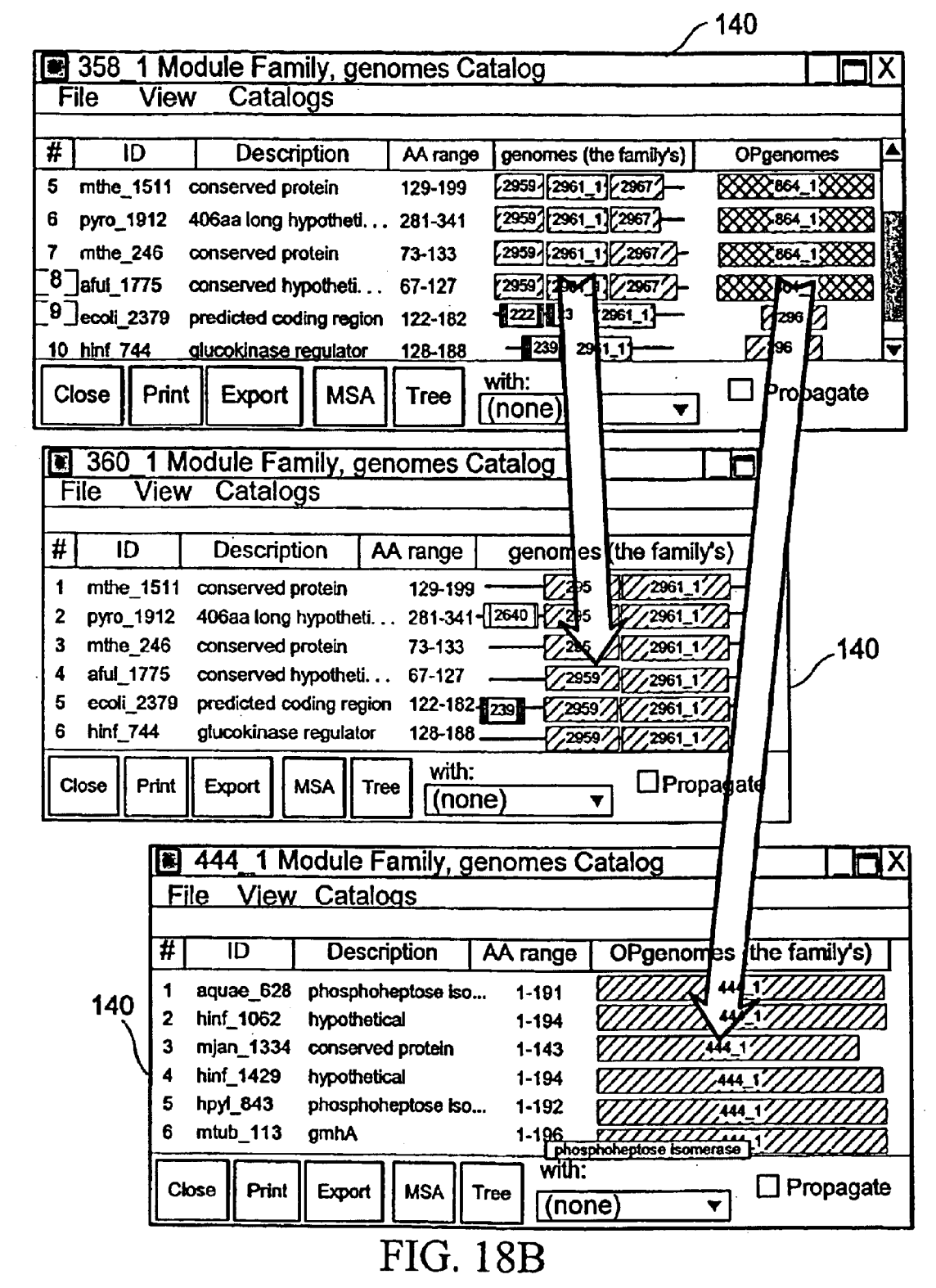

FIG. 18A depicts the MFS window 140 for one catalog. From the menu bar, additional catalog views may be selected. In this example, both the genomes and OPgenomes catalogs are chosen to be viewed as shown in FIG. 18B. This view depicts the MFS window with two catalogs. From this window the user can begin progressive query-marking activity by selecting modules of interest and viewing them in the MFS windows.

EXAMPLE 4

Figure 19:
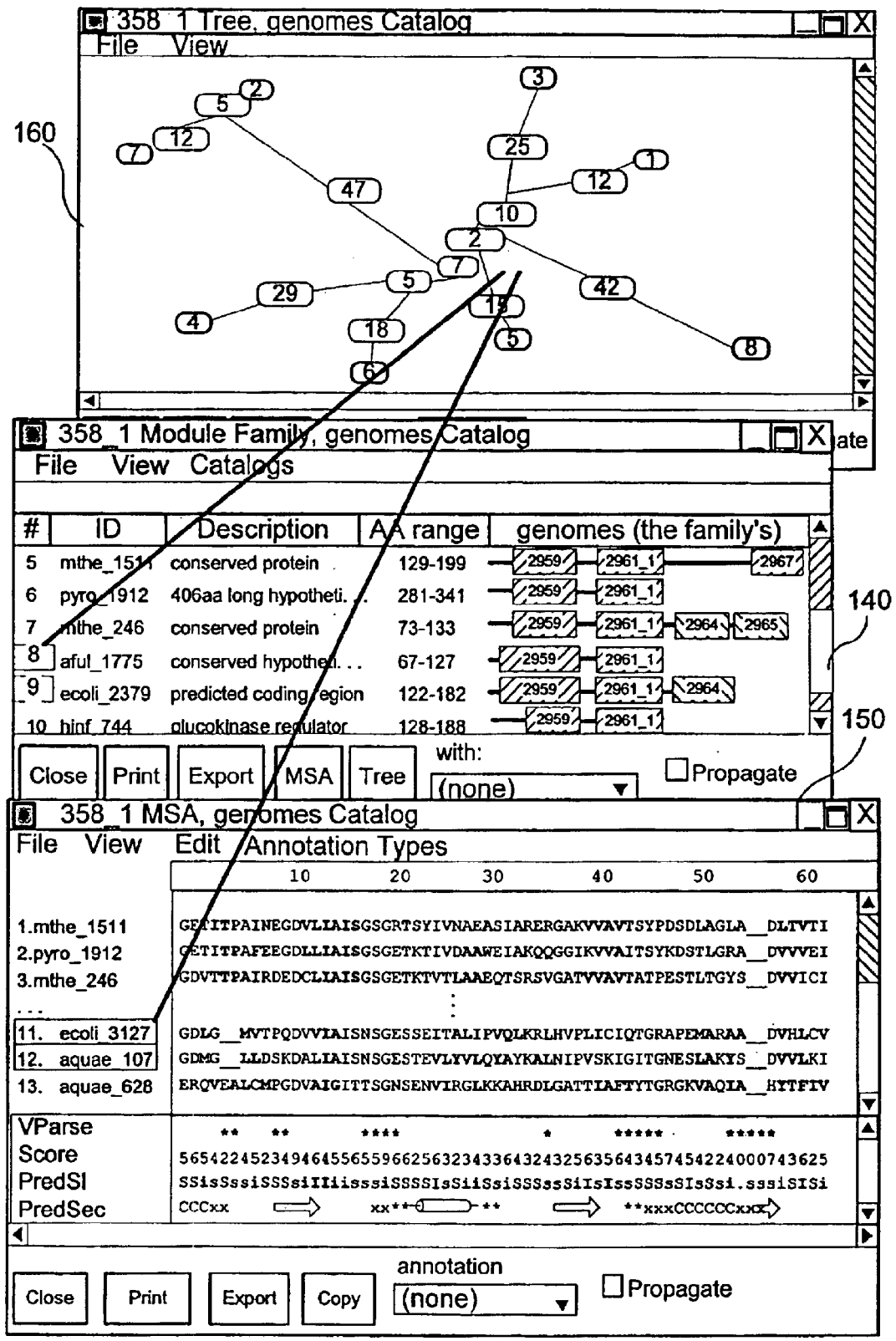
FIG. 19 depicts the screen display for the evolutionary tree window as linked to the MFS window and MSA window with highlighted selections propagated throughout.

FIG. 19 depicts the screen display for the evolutionary tree window 160 as linked to the MFS window 140 and MSA window 150 with highlighted selections propagated throughout. Highlighting a section of the tree will automatically propagate the highlighting to the other windows (MSA and MFS) for the selected sequences.

EXAMPLE 5

Figure 20:
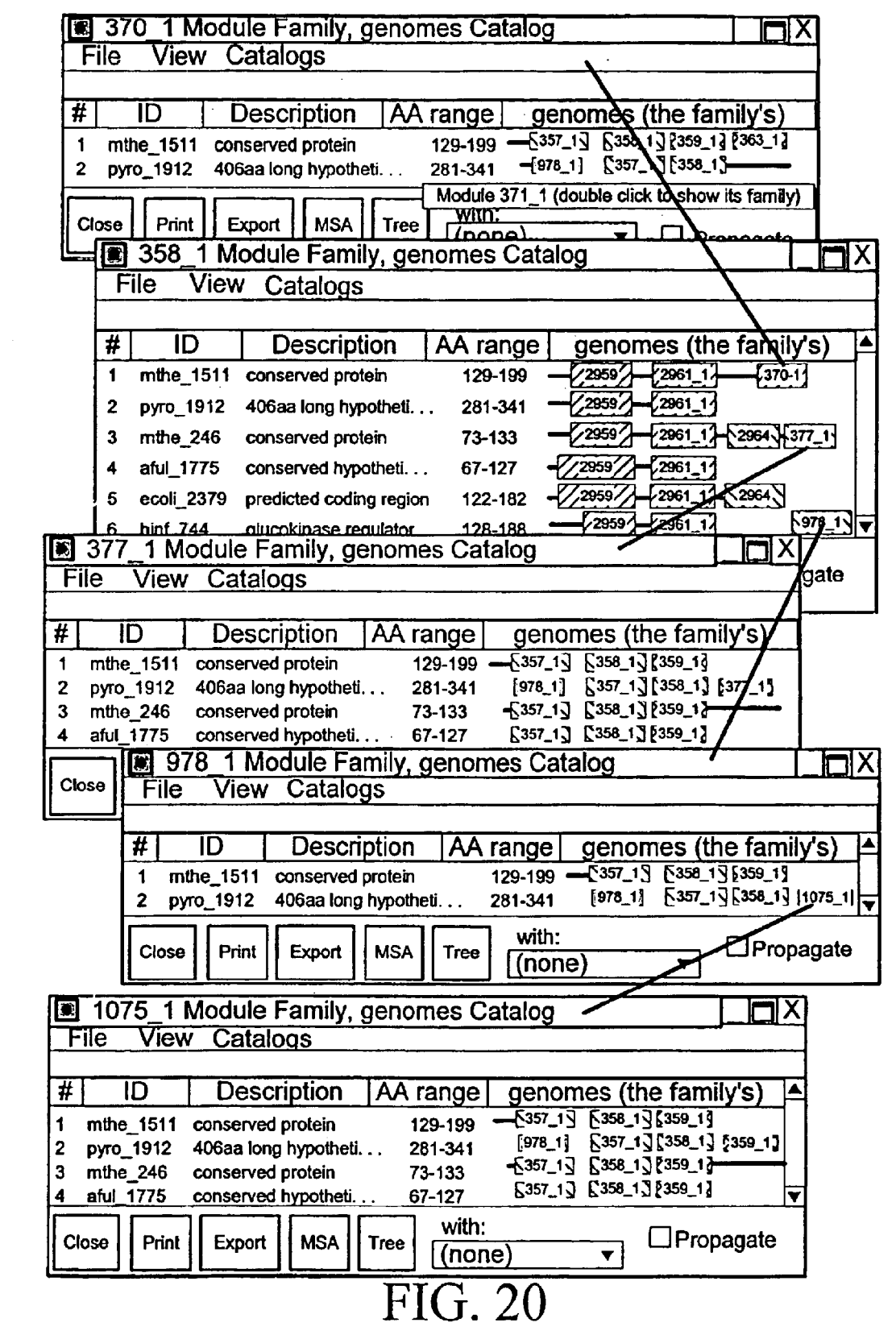

FIG. 20 depicts the screen displays showing interactive and progressive query-making activity across multiple MFS windows 140. Beginning, for example, with the 358_1 module MFS window, the user can select the 377_1 for display, the 978_1 for display, and the 371_1 for display (simultaneously). The windows can be closed or moved about the screen as desired. Thereafter, the user can continue to select displays from the resulting windows, e.g., the user can select the 1075_1 module from the 978_1 MFS window for display, and so on. Progressive querying can be continued through level upon level. Of course, from each MFS window 140, the MSA 150 of FIG. 14, evolutionary tree 160 of FIG. 15, or database entry (not shown) can be displayed as depicted in the flowchart of FIG. 6.

It should be understood that the examples and embodiments described herein are for illustrative purposes only and that various modifications or changes in light thereof will be suggested to persons skilled in the art and are to be included within the spirit and purview of this application and the scope of the appended claims. All patents, patent applications, provisional applications, and publications referred to or cited herein, or for which a claim for benefit of priority has been made, are incorporated by reference in their entirety to the extent they are not inconsistent with the explicit teachings of this specification.

What is claimed is:

1. A method of navigating a biological database in computer storage, the biological database including at least one catalog containing an organized body of related biological data, the method comprising the acts of:
    selecting at least one catalog;
    searching the catalog by entering search criteria into a computer and thereby display on the computer a list of search results including at least one module representing a region of a protein sequence;
    selecting a first module of interest from the list of search results;
    displaying on the computer a family of all protein sequences in the database having the first module of interest, each protein sequence also being associated with a graphical representation of all modules of the protein sequence; and
    displaying a multiple sequence alignment for the family of protein sequences in a separate display area, the multiple sequence alignment presenting an amino-acid-by-amino-acid relationship between protein sequences in the same family.

2. The method of claim 1 wherein portions of the multiple sequence alignment are identified as being either hydrophobic, hydrophilic, or amphiphilic residues.

3. The method of claim 1 wherein portions of the multiple sequence alignment are identified as secondary structure breaking positions.

4. The method of claim 1 wherein portions of the multiple sequence alignment are identified as predicated surface/interior residues.

5. The method of claim 1 wherein the multiple sequence alignment shows a predicated secondary structure.

6. The method of claim 1 wherein the multiple sequence alignment shows an experimentally determined secondary structure.

7. The method of claim 1 wherein a selection in any one of the display areas results in a propagation of the selection to the other display areas.

8. The method of claim 1 and further comprising selecting a second module of interest from the display area of the first family and displaying a second family of protein sequences having the second module of interest, each protein sequence also being associated with a graphical representation of all modules of the protein sequence.

9. A method of navigating a biological database in computer storage, the biological database including at least one catalog containing an organized body of related biological data, the method comprising the acts of:
    selecting at least one catalog;
    searching the catalog by entering search criteria into a computer and thereby display on the computer a list of search results including at least one module representing a region of a protein sequence;
    selecting a first module of interest from the list of search results;
    displaying on the computer a family of all protein sequences in the database having the first module of interest, each protein sequence also being associated with a graphical representation of all modules of the protein sequence; and
    displaying a biological tree for the family of protein sequences in a separate display area, the biological tree presents distance relationships between protein sequences in the family.

10. The method of claim 9 wherein the biological tree presents patterns of similarity and divergence between protein sequences in the family.

11. The method of claim 9 wherein the biological tree is constructed using PAM distances between protein sequences in the family.

12. The method of claim 9 wherein the biological tree presents a ratio of expressed changes at the DNA level to the rate of silent changes between protein sequences in the family.

13. The method of claim 12 wherein the ratio is presented with separate coloring schemes indicating branches above or below a user selectable threshold.

14. The method of claim 9 wherein a selection in any one of the display areas results in a propagation of the selection to the other display areas.

15. A method of navigating a biological database in computer storage, the biological database including at least one catalog containing an organized body of related biological data, the method comprising the acts of:
- selecting at least one catalog;
- searching the catalog by entering search criteria into a computer and thereby display on the computer a list of search results including at least one module representing a region of a protein sequence;
- selecting a first module of interest from the list of search results;
- displaying on the computer a first family of all protein sequences in the database having the first module of interest, each protein sequence also being associated with a graphical representation of all modules of the protein sequence; and
- displaying the search criteria as a member of the family.

16. A method of navigating a biological database in computer storage, the biological database including at least one catalog containing an organized body of related biological data, the method comprising the acts of:
- selecting at least one catalog;
- searching the catalog by entering search criteria into a computer and thereby display a list of search results including at least one module representing a region of a protein sequence;
- selecting a first module of interest from the list of search results;
- displaying on the computer a first family of all protein sequences in the database having the first module of interest, each protein sequence also being associated with a graphical representation of all modules of the protein sequence; and
- selecting a second module of interest from the display area of the first family of protein sequences and displaying a second family of protein sequences including all protein sequences having the second module of interest, each protein sequences also being associated with a graphical representation of all modules of the protein sequence.

17. The method of claim 16 and further comprising displaying a multiple sequence alignment for the first or second family in a separate display area.

18. The method of claim 17 wherein the multiple sequence alignment presents an amino-acid by amino-acid relationship between protein sequences which are in the same family.

19. The method of claim 17 wherein portions of the multiple sequence alignment are identified as being either hydrophobic, hydrophilic, or amphiphilic residues.

20. The method of claim 17 wherein portions of the multiple sequence alignment are identified as secondary structure breaking positions.

21. The method of claim 17 wherein portions of the multiple sequence alignment are identified as predicated surface/interior residues.

22. The method of claim 17 wherein the multiple sequence alignment shows a predicted secondary structure.

23. The method of claim 17 wherein the multiple sequence alignment shows an experimentally determined secondary structure.

24. The method of claim 17 wherein a selection in any one of the display areas results in a propagation of the selection to the other display areas.

25. The method of claim 16 and further comprising displaying a biological tree for the first or second family.

26. The method of claim 25 wherein the biological tree presents distance relationships between protein sequences in the family.

27. The method of claim 25 wherein the biological tree presents patterns of similarity and divergence between protein sequences in the family.

28. The method of claim 25 wherein the biological tree is constructed using PAM distances between protein sequences in the family.

29. The method of claim 25 wherein the biological tree presents a ratio of expressed changes at the DNA level to the rate of silent changes between protein sequences in the family.

30. The method of claim 29 wherein the ratio is presented with separate coloring 31. The method of claim 25 wherein a selection in any one of the display areas results in a propagation of the selection to the other display areas.

32. The method of claim 16 and further comprising displaying a multiple sequence alignment or a biological tree for the first and second family simultaneously.

33. The method of claim 16 wherein like modules for each protein sequence of the family are positionally aligned and visibly distinguished.

34. A method of performing a computerized protein sequence analysis to detect similarities in the composition of different proteins, the method comprising:
- accessing a biological database in computer storage, the biological database incorporating data of at least one pre-existing database and having pre-computed families described by a probabilistic sequence;
- navigating the biological database with a graphical user interface to query the database for a list of search results;
- displaying the list of search results including at least one module representing a region of a protein sequence; and
- navigating the biological database with the graphical user interface to select one or more of the modules for representation on a computer as a family;
- wherein multiple families are presented in separate display areas.

35. The method of claim 34 wherein a selection in any one of the display areas results in a propagation of the selection to the other display areas.

36. The method of claim 34 wherein the query criteria is displayed as a member of the family.

37. A method of performing a computerized protein sequence analysis to detect similarities in the composition of different proteins, the method comprising:
- accessing a biological database in computer storage, the biological database incorporating data of at least one pre-existing database and having pre-computed families described by a probabilistic sequence;
- navigating the biological database with a graphical user interface to query the database for a list of search results;
- displaying the list of search results including at least one module representing a region of a protein sequence; and
- navigating the biological database with the graphical user interface to select one or more of the modules for representation on a computer as a multiple sequence alignment;
- wherein multiple sequence alignments are presented in separate display areas.

38. The method of claim 37 wherein a selection in any one of the display areas results in a propagation of the selection to the other display areas.

39. The method of claim 37 wherein the query criteria is displayed in the multiple sequence alignment.

40. A method of performing a computerized protein sequence analysis to detect similarities in the composition of different proteins, the method comprising:

accessing a biological database in computer storage, the biological database incorporating data of at least one pre-existing database and having pre-computed families described by a probabilistic sequence;

navigating the biological database with a graphical user interface to query the database for a list of search results;

displaying the list of search results including at least one module representing a region of a protein sequence; and navigating the biological database with the graphical user interface to select one or more of the modules for representation on a computer as a biological tree;

wherein multiple biological trees are presented in separate display areas.

41. The method of claim 40 wherein a selection in any one of the display areas results in a propagation of the selection to the other display areas.

42. The method of claim 40 wherein the query criteria is displayed in the biological tree.

* * * * *